US007851194B2

(12) United States Patent
Markoff et al.

(10) Patent No.: US 7,851,194 B2
(45) Date of Patent: Dec. 14, 2010

(54) WEST NILE VIRUSES WITH MUTATIONS IN THE 3' TERMINAL STEM AND LOOP SECONDARY STRUCTURE FOR USE AS LIVE VIRUS VACCINES

(75) Inventors: Lewis Markoff, Bethesda, MD (US); Li Yu, Gaithersburg, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 240 days.

(21) Appl. No.: 11/629,560

(22) PCT Filed: Jun. 14, 2005

(86) PCT No.: PCT/US2005/020737

§ 371 (c)(1), (2), (4) Date: Sep. 17, 2008

(87) PCT Pub. No.: WO2006/036233

PCT Pub. Date: Apr. 6, 2006

(65) Prior Publication Data

US 2009/0028900 A1    Jan. 29, 2009

Related U.S. Application Data

(60) Provisional application No. 60/579,386, filed on Jun. 14, 2004.

(51) Int. Cl.
| | |
|---|---|
| C12N 7/00 | (2006.01) |
| C12N 7/04 | (2006.01) |
| C12N 15/86 | (2006.01) |
| A61K 39/12 | (2006.01) |
| A61K 39/295 | (2006.01) |

(52) U.S. Cl. .................. 435/235.1; 435/236; 435/5; 435/471; 424/199.1; 424/218.1

(58) Field of Classification Search .................. None
See application file for complete search history.

(56) References Cited

U.S. PATENT DOCUMENTS 6,685,948 B1    2/2004    Zeng et al.

FOREIGN PATENT DOCUMENTS

| WO | WO 00/14245 | * | 3/2000 |
| WO | WO 02/074963 | * | 9/2002 |
| WO | WO 02/074963 A1 | | 9/2002 |
| WO | WO 02/095075 | * | 11/2002 |
| WO | WO 03/059384 A1 | | 7/2003 |
| WO | WO 2005/049815 A1 | | 6/2005 |

OTHER PUBLICATIONS

Lo et al (Journal of Virology 77:10004-10014, 2003).*
Chambers et al (Journal of General Virology 79:2375-2380, 1998).*
Pugachev et al (International Journal for Parasitology 33:567-582, 2003).*
Men et al (Journal of Virology 70:3930-3937, 1996).*
Butrapet et al. Journal of Virology, Apr. 2000, p. 3011-3019 vol. 74, No. 7.*
Monath et al .Journal of Virology, Feb. 2002, p. 1932-1943 vol. 76, No. 4.*
Guirakhoo et al. Journal of Virology, Sep. 2004, p. 9998-10008 vol. 78, No. 18.*
Arroyo, J. et al. (2001) "Yellow fever vector live-virus vaccines: West Nile virus vaccine development" *Trends Mol. Med.* 7:350-354.
Bartel, D.P. et al. (1991) "HIV-1 Rev regulation involves recognition of non-Watson-Crick base pairs in the viral RNA." *Cell* 67:529-536.
Beasley, D.W.C. et al. (2002) "Mouse neuroinvasive phenotype of West Nile virus strains varies depending upon virus genotype." *Virology* 296:17-23.
Blackwell, J. et al. (1995) "BHK cell proteins that bind to the 3' stem-loop structure of the West Nile virus genome RNA." *J. Virol.* 69:5650-5658.
Blackwell, J.L. et al. (1997) "Translation elongation factor-1 alpha interacts with the 3' stem-loop region of West Nile virus genomic RNA." *J. Virol.* 71:6433-6444.
Brinton, M.A. (2002) "The molecular biology of West Nile Virus: a new invader of the western hemisphere." *Ann. Rev. Microbiol.* 56:371-402.
Brinton, M.A. et al. (1986) "The 3'-nucleotides of flavivirus genomic RNA form a conserved secondary structure." *Virology* 153:113-121.
Calisher, C.H. et al. (1989) "Antigenic relationships between flaviviruses as determined by cross-neutralization tests with polyclonal antisera." *J. Gen. Virol.* 70:37-43.
Centers for Disease Control and Prevention. (1999) "Outbreak of West Nile virus encephalitis—New York, 1999." *Morb. Mortal. Wkly. Rep.* 48:845-849.
Centers for Disease Control and Prevention. (2002) "Provisional surveillance summary of the West Nile virus epidemic—UnitedStates, Jan.-Nov. 2002." *Morb. Mortal. Wkly. Rep.* 51:1129-1133.
Chapman, M.R. et al. (1999) "A minimal RNA promoter for minus-strand RNA synthesis by the brome mosaic virus polymerase complex." *J. Mol. Biol.* 286:709-720.
Chen, C.-J. et al. (1997) "RNA protein interactions: involvement of NS3, NS5, and 3' noncoding regions of Japanese encephalitis virus genomic RNA." *J. Virol.* 71:3466-3473.

(Continued)

*Primary Examiner*—Mary E Mosher
(74) *Attorney, Agent, or Firm*—Edwards Angell Palmer & Dodge LLP; Peter F. Corless; Christine C. O'Day

(57) ABSTRACT

The invention provides West Nile (WN) viruses and chimeric WN viruses having one or more mutations in the 3' terminal stem loop secondary structure (3'SL) that results in decreased neurovirulence, methods of making such WN viruses, and methods for using these WN viruses to prevent or treat WN virus infection.

18 Claims, 12 Drawing Sheets

OTHER PUBLICATIONS

De Nova-Campo, M. et al. (2002) "Translation elongation factor-1α, La, and PTB interact with the 3'-untranslated region of dengue 4 virus RNA." *Virology* 295:337-347.

Grange, T. et al. (1985) "Stable secondary structures at the 3'-end of the genome of yellow fever virus (17D vaccine strain)." *FEBS Lett.* 188:159-163.

Herold, J. et al. (2001) "Poliovirus RNA replication requires genome circularization through a protein-protein bridge." *Mol. Cell* 7:581-591.

Huang, P. et al. (2001) "Heterogeneous nuclear ribonucleoprotein A1 binds to the 3'-untranslated region and mediates potential 5'-3'-end cross talks of mouse hepatitis virus RNA". *J. Virol.* 75:5009-5017.

International Preliminary Report on Patentability from PCT/US2005/020737, (Dec. 14, 2006).

Irie, K. et al. (1989) "Sequence analysis of cloned dengue virus type 2 genome (New Guinea-C strain)." *Gene* 75:197-211.

Ito, T. et al. (1997) "Determination of the secondary structure of and cellular protein binding to the 3'-untranslated region of the hepatitis C virus RNA genome." *J. Virol.* 71:8698-8706.

Khromykh, A.A. et al. (1998) "trans-Complementation of flavivirus RNA polymerase gene NS5 by using Kunjin virus replicon-expressing BHK cells." *J. Virol.* 72:7270-7279.

Khromykh, A.A. et al. (1999) "trans-Complementation analysis of the flavivirus Kunjin ns5 gene reveals an essential role for translation of its N-terminal half in RNA replication." *J. Virol.* 73:9247-9255.

Khromykh, A.A. et al. (2000) "*cis*- and *trans*-acting elements in flavivirus RNA replication." *J. Virol.* 74:3253-3263.

Khromykh, A.A. et al. (2003) "Significance in replication of the terminal nucleotides of the Flavivirus genome." *J. Virol.* 77:10623-10629.

Kolb, F.A. et al. (2001) "Bulged residues promote the progression of a loop-loop interaction to a stable and inhibitory antisense-target RNA complex." *Nucleic Acids Res.* 29:3145-3153.

Kummerer, B.M. et al. (2002) "Mutations in the yellow fever virus nonstructural protein NS2A selectively block production of infectious particles." *J. Virol.* 76:4773-4784.

Lanciotti, R.S. et al. (1999) "Origin of the West Nile virus responsible for an outbreak of encephalitis in the northeastern United States." *Science* 286:2333-2337.

Lim, F. et al. (2002) "RNA recognition site of PP7 coat protein." *Nucleic Acids Res.* 30:4138-4144.

Markoff, L. et al. (2002) "Derivation and characterization of a dengue type 1 host range-restricted mutant virus that is attenuated and highly immunogenic in monkeys." *J. Virol.* 76:3318-3328.

Matzura, O. et al. (1996) "RNAdraw: an integrated program for RNA structure calculation and analysis under 32-bit Microsoft Windows." *Comput. Appl. Biol. Sci.* 12:247-249.

Men, R. et al. (1996) "Dengue type 4 virus mutants containing deletions in the 3' noncoding region of the RNA genome: analysis of growth restriction in cell culture and altered viremia pattern and immunogenicity in rhesus monkeys." *J. Virol.* 70:3930-3937.

Mohan, P.M. et al. (1991) "Detection of stable secondary structure at the 3' terminus of dengue virus type 2 RNA." *Gene* 108:185-191.

Nakhasi, H.L. et al. (1990) "Specific high-affinity binding of host cell proteins to the 3' region of rubella virus RNA." *New Biol.* 2:255-264.

Osman, T.A. et al. (2000) "Role of the 3' tRNA-like structure in tobacco mosaic virus minus-strand RNA synthesis by the viral RNA-dependent RNA polymerase *in vitro*." *J. Virol.* 74:11671-11680.

Pogue, G.P. et al. (1996) "Autoantigens interact with *cis*-acting elements of rubella virus RNA." *J. Virol.* 70:6269-6277.

Rice, C.M. et al. (1985) "Nucleotide sequence of yellow fever virus: implications for flavivirus gene expression and evolution." *Science* 229:726-733.

Sampathkumar, P. (2003) "West Nile virus: epidemiology, clinical presentation, diagnosis, and prevention." *Mayo Clin. Proc.* 78:1137-1144.

Schuppli, D. et al. (1998) "A branched stem-loop structure in the M-site of bacteriophage Qβ RNA is important for template recognition by Qβ replicase holoenzyme." *J. Mol. Biol.* 283:585-593.

Shi, P.-Y. et al. (1996) "Evidence for the existence of a pseudoknot structure at the 3' terminus of the flavivirus genomic RNA." *Biochemistry* 35:4222-4230.

Sikorski, R.S. et al. (1989) "A system of shuttle vectors and yeast host strains designed for efficient manipulation of DNA in *Saccharomyces cerevesiae*." *Genetics* 122:19-27.

Stern, S. et al. (1986) "Localization of the binding site for protein S4 on 16S ribosomal RNA by chemical and enzymatic probing and primer extension." *J. Mol. Biol.* 192:101-110.

Ta, M. et al. (2000) "Mov34 protein from mouse brain interacts with the 3' noncoding region of Japanese encephalitis virus." *J. Virol.* 74:5108-5115.

Tan, B.H. et al. (1996) "Recombinant dengue type 1 virus NS5 protein expressed in *Escherichia coli* exhibits RNA-dependent RNA polymerase activity." *Virology* 216:317-325.

Weeks, K.M. et al. (1991) "RNA recognition by Tat derived peptides: interaction in the major groove?" *Cell* 66:577-588.

Wengler, G. et al. (1986) "Analysis of structural properties which possibly are characteristic for the 3'-terminal sequence of the genome RNA of flaviviruses." *J. Gen. Virol.* 67:1183-1188.

Wu, H.-N. et al. (1987) "Role of a bulged A residue in a specific RNA-protein interaction." *Biochemistry* 26:8221-8227.

Yamshchikov, V.F. et al. (2001) "An infectious clone of the West Nile flavivirus." *Virology* 281:294-304.

Yu, L. et al. (2005) "The topology of bulges in the long stem of the flavivirus 3' stem-loop is a major determinant of RNA replication competence." *J. Virol.* 79:2309-2324.

Zeng, L. et al. (1998) "Identification of specific nucleotide sequences within the conserved 3'-SL in the dengue type 2 virus genome required for replication." *J. Virol.* 72:7510-7522.

\* cited by examiner

```
                              SEQUENCE LISTING

<160> NUMBER OF SEQ ID NOS: 46

<210> SEQ ID NO 1
<211> LENGTH: 93
<212> TYPE: RNA
<213> ORGANISM: Dengue Virus

<400> SEQUENCE: 1
cugggaaaga ccagagaucc ugcugucucc ucagcaucau uccaggcaca gaacgccaga      60
aaauggaaug gugcuguuga aucaacaggu ucu                                   93

<210> SEQ ID NO 2
<211> LENGTH: 95
<212> TYPE: RNA
<213> ORGANISM: West Nile Virus

<400> SEQUENCE: 2
ccugggauag acuagggau cuucugcucu gcacaaccag ccacacggca cagugcgccg       60
acaauggugg cuggguggugc uagaacacag gaucu                                95

<210> SEQ ID NO 3
<211> LENGTH: 84
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 3
agauccugcu gucuccugca caaccagcca cacggcacag ugcgccgaca augguggcug      60
guggugcuug aaucaacagg uucu                                             84

<210> SEQ ID NO 4
<211> LENGTH: 74
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 4
ggaucuucug cucucagcau cauuccaggc acagaacgcc agaaaaugga auggugcugu      60
agaacacagg aucu                                                        74

<210> SEQ ID NO 5
<211> LENGTH: 78
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 5
ggaucuucug cucugcacaa ccagccacag gcacagaacg ccagaaaaug uggcuggugg      60
ugcuagaaca caggaucu                                                   78

<210> SEQ ID NO 6
<211> LENGTH: 84
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 6
agauccugcu gucuccugca caaccagcca cacggcacag ugcgccgaca augguggcug      60
guggugcuug aaucaacagg uucu                                            84

<210> SEQ ID NO 7
<211> LENGTH: 83
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 7
agauccugcu gucuccugca caaccagcca cacggcacag ugcgccgaca augguggcug      60
guggugcuug aaucaacaga auc                                             83

<210> SEQ ID NO 8
<211> LENGTH: 86
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 8
agauuccugc ugucuccugc acaaccagcc acacggcaca gugcgccgac aaugguggcu      60
gguggugcuu gaaucaacag guaucu                                          86

<210> SEQ ID NO 9
<211> LENGTH: 82
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 9
agauccugcu gccuccugca caaccagcca cacggcacag ugcgccgaca augguggcug      60
gcggugcuug aaucaacagg uu                                              82

<210> SEQ ID NO 10
<211> LENGTH: 84
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 10
```

```
agauccugcu gucuccugca caaccagcca cacggcacag ugcgccgaca augguggcug    60
guggugcuug aaucaacagg uucu                                          84
```

<210> SEQ ID NO 11
<211> LENGTH: 74
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 11

```
agauccugcu gucuccuacc agccacacgg cacagugcgc cgacaauggu ggcugguuug    60
aaucaacagg uucu                                                     74
```

<210> SEQ ID NO 12
<211> LENGTH: 74
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 12

```
ggaucuucug cucucagcau cauuccaggc acagaacgcc agaaaaugga auggugcugu    60
agaacacagg aucu                                                     74
```

<210> SEQ ID NO 13
<211> LENGTH: 84
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 13

```
ggaucuucug cucugcacac agcaucauuc caggcacaga acgccagaaa auggaauggu    60
gcugggugcu agaacacagg aucu                                          84
```

<210> SEQ ID NO 14
<211> LENGTH: 84
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 14

```
ggaucuucug cucugcacac agcaucauuc caggcacaga acgccagaaa auggaauggu    60
gcugggugcu agaacacagg aucu                                          84
```

<210> SEQ ID NO 15
<211> LENGTH: 82
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 15

```
ggaucuucug cucugcacaa gcaucauucc aggcacagaa cgccagaaaa uggaauggug    60
cuggugcuag aacacaggau cu                                            82
```

```
<210> SEQ ID NO 16
<211> LENGTH: 76
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 16
ggaucuucug cucugcacaa ucauuccagg cacagaacgc cagaaaaugg aaugguggug    60
cuagaacaca ggaucu                                                    76

<210> SEQ ID NO 17
<211> LENGTH: 80
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 17
ggaucuucug cucucuccuc accagccaca cggcacagug cgccgacaua gguggcuggu    60
guugaaugaa cacaggaucu                                                80

<210> SEQ ID NO 18
<211> LENGTH: 79
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 18
agauccucug cucugcacaa ccagccacac ggcacagugc gccgacaaug guggcuggug    60
gugcuagaac acagguucu                                                 79

<210> SEQ ID NO 19
<211> LENGTH: 79
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 19
ggaucuucug cucugcacca ccagccacac ggcacagugc gccgacauag guggcuggug    60
gugcuagaac acaggaucu                                                 79

<210> SEQ ID NO 20
<211> LENGTH: 79
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 20
ggaucuucug cucugcacaa ccagccacac ggcacagugc gccgacauag guggcugguu    60
gugcuagaac acaggaucu                                                 79

<210> SEQ ID NO 21
<211> LENGTH: 79
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 21
ggaucuucug cucugcacua ccagccacac ggcacagugc gccgacauag guggcugguu    60
gugcuagaac acaggaucu                                                 79

<210> SEQ ID NO 22
<211> LENGTH: 93
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 22
cugggagaga ccagagaucc ugcugucucu acagcaucau uccaggcaca gaacgccaga    60
aaauggaaug gugcuguuga aucaacaggu ucu                                 93

<210> SEQ ID NO 23
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
accatttcac ggaactgatc atg                                            23

<210> SEQ ID NO 24
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
atgggtacca tttaggtgac actatagagt agttcgcctg tgagctgca                49

<210> SEQ ID NO 25
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
tgttctagaa ccaccagcca cctatgtcgg cgcac                               35

<210> SEQ ID NO 26
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
cctttctaga gatcctgtgt tctcgcacca ccagcc                              36
```

-continued

```
<210> SEQ ID NO 27
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
cctagtctat cccaggtgtc aatatgc                                        27

<210> SEQ ID NO 28
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
agtagttcgc ctgtgtgaca aacttag                                        27

<210> SEQ ID NO 29
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
acttccgcac cggagctctt gcc                                            23

<210> SEQ ID NO 30
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
gtggggaaag ccaatacacc aagtc                                          25

<210> SEQ ID NO 31
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
ctttgatgag gcttccaact ccaacc                                         26

<210> SEQ ID NO 32
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
taagcttcac caacacttca aatgtg                                         26
```

<210> SEQ ID NO 33
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
tgaggtttgg taccgaatgg gaagtc                                          26

<210> SEQ ID NO 34
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
agagtagatg tgaggctgga tgatg                                           25

<210> SEQ ID NO 35
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
catcgtggtc acattggtga tagtg                                           25

<210> SEQ ID NO 36
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
gccagctccc ttgtgaatgg ggtag                                           25

<210> SEQ ID NO 37
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
gttgcagctg tcattggatg gatgc                                           25

<210> SEQ ID NO 38
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
gcccgacgac cgttgaatct catgg                                           25

<210> SEQ ID NO 39

<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
gccgtcaaga acaacatggc                                           20

<210> SEQ ID NO 40
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
cttcccattc ggtaccaaac ctcagc                                    26

<210> SEQ ID NO 41
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
cttcccattc ggtaccaaac ctcagc                                    26

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
aacgaagtgt tgatagtctg                                           20

<210> SEQ ID NO 43
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
cttgatctgc ggccggccac ggcatgg                                   27

<210> SEQ ID NO 44
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
cagccacatc tgcgcgtatg acttcg                                    26

<210> SEQ ID NO 45
<211> LENGTH: 28

-continued

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
tgtcaatatg ctgtttcttt tggtgttt                                          28

<210> SEQ ID NO 46
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
actcccgctg acactggcca cggaacggtg                                        30
```

WEST NILE VIRUSES WITH MUTATIONS IN THE 3' TERMINAL STEM AND LOOP SECONDARY STRUCTURE FOR USE AS LIVE VIRUS VACCINES

RELATED APPLICATIONS

This application is a U.S. National Phase of International Application No. PCT/US2005/020737, filed Jun. 14, 2005, designating the U.S. and published in English as WO 2006/036233 on Apr. 6, 2006, which claims the benefit of U.S. Provisional Patent Application No. 60/579,386 filed Jun. 14, 2004, the entire disclosure of which is hereby expressly incorporated by reference.

SEQUENCE LISTING

The instant application contains a Sequence Listing which has been submitted via EFS-Web and is hereby incorporated by reference in its entirety. Said ASCII copy, created on Dec. 9, 2009, is named 84321479.txt, and is 12,526 bytes in size.

BACKGROUND OF THE INVENTION

The flavivirus West Nile (WN) virus historically circulated only in the Middle East, Far East, Africa, and southern Europe. The primary life cycle requires birds or horses and local arthropod vectors. In humans, WN virus typically causes a severe fever-arthralgia-rash syndrome but also has a propensity to invade the CNS and cause meningoencephalitis or encephalitis, especially in the elderly (Beasley, D. L. et al. 2002 *Virology* 296:17-23; Sampathkumar P. 2003 *Mayo Clin Proc* 78:1137-1143). In the summer of 1999, WN virus infections of birds and humans were detected in New York City, indicating the presence of this pathogen on the American continent for the first time (Centers for Disease Control and Prevention 1999 *MMWR Morb Mortal Wkly Rep* 48:845-849; Lanciotti, R. S. et al. 1999 *Science* 286:2333-2337). Since 1999, disease has recurred annually in the United States, reaching epidemic proportions in focal areas of the Eastern and mid-western states during 2002 (Centers for Disease Control and Prevention 2002 *MMWR Morb Mortal Wkly Rep* 51:1129-1133). WN virus continues to pose a serious threat to the public health, since the vector species are present throughout the North American continent, and since there is no vaccine available.

Flavivirus positive-strand genome RNA is about 10.5 kb in total length and contains a single long open reading frame (ORF), encoding three major viral structural proteins and at least seven non-structural (NS) proteins. The ORF is flanked by a 5' noncoding region (NCR) which is about 100 nucleotides (nt) in length and by a 3'-NCR which is 400 to 800 nucleotides in length (Lindenbach, B. D. and Rice C. M 2001 *in Fields Virology*, 4$^{th}$ ed., Knipe, D. M. and Howley, P. M. (eds.), Lippincott Williams and Wilkins, New York, pp 991-1041). The 3'-terminal ~100 nucleotides of the 3'-NCR form two adjacent small and large stem and loop structures, here referred to collectively as the 3'SL (Brinton, M. A. et al. 1986 *Virology* 153:113-121; Grange, T. M. et al. 1985 *FEBS Lett* 188:159-163; Irie, K. et al. 1989 *Gene* 75:197-211; Men, R. et al. 1996 *J Virol* 70:3930-3937; Mohan, P. M. and Padmanabhan, R. 1991 *Gene* 108:185-191; Rice, C. M. et al. 1985 *Science* 229:726-735; Wengler, G. and Castle, E. 1986 *J Gen Virol* 67:1183-1188). This secondary structure is conserved among all flavivirus genomes. The 3'SL is essential for virus replication (Men, R. et al. 1996 *J Virol* 70:3930-3937; Zeng, L. et al. 1998 *J Virol* 72:7510-7522) and has specific affinity for host cellular proteins (Blackwell, J. L. and Brinton, M. A. 1996 *J Virol* 69:5650-5658; Blackwell, J. L. and Brinton, M. A. 1997 *J Virol* 71:6433-6444; De Nova-Campo, M. et al. 2002 *Virology* 295:337-347; Ito, T. and Lai, M. M. 1997 *J Virol* 71:8698-8706; Ta, M. and Vrati, S. 2000 *J Virol* 74:5108-5115) and for viral NS proteins of the replication complex (Chen, C.-J. et al. 1997 *J Virol* 71:3466-3473), including NS5 (Tan, B. H. et al. 1996 *Virology* 216:317-325), the viral RNA-dependent RNA polymerase.

SEGUE TO THE INVENTION

In the present study, we modified a WN infectious DNA such that all or segments of the wild-type (wt) WN 3'SL nucleotide sequence were replaced by analogous dengue virus serotype 2 (DEN2) 3'SL nucleotide sequences. In addition, relevant point mutations were created in the nucleotide sequence of the WN 3'SL. wt and mutant WN RNAs derived by in vitro transcription were transfected into BHK and Vero cells to determine the replication phenotypes of resultant WN viruses. A mutant WN virus RNA containing a substitution of the WN 3'SL nucleotide sequence by the DEN2 3'SL nucleotide sequence failed to initiate negative strand RNA synthesis in transfected cells. Further analysis of the replication phenotypes of 3'SL mutant WN virus RNAs revealed that a bulge within the top portion of the long stem in the WN virus 3'SL was essential for WN virus replication. In addition, the introduction of a second bulge into the lower part of the long stem of the WN virus 3'SL was an enhancer of replication of WN virus in cultured mosquito cells but had no significant effect on virus replication in monkey kidney cells. The results of an earlier study of the DEN2 3'SL (Zeng, L. et al. 1998 *J Virol* 72:7510-7522) and those of the present study of the WN virus 3'SL taken together were consistent with the unifying hypothesis that bulges and their specific locations in the long stems of both the DEN2 and WN virus 3'SL are critical determinants of RNA replication competence at the level of initiation of translation and/or negative strand RNA synthesis. Most likely, bulges are critical sites for binding of viral and cellular proteins to form the flavivirus replication complex.

SUMMARY OF THE INVENTION

The invention provides West Nile (WN) viruses and chimeric WN viruses having one or more mutations in the 3' terminal stem loop secondary structure (3'SL) that results in decreased neurovirulence, methods of making such WN viruses, and methods for using these WN viruses to prevent or treat WN virus infection.

BRIEF DESCRIPTION OF THE DRAWINGS

FIG. 1. The 3' terminal 93-nucleotide (nt) sequence of the DEN2 strain New Guinea C (NGC) 3'SL is shown on the left (SEQ ID NO: 1), and the 95-nt sequence of the WN virus strain 956 3'SL is shown on the right (SEQ ID NO: 2). Nucleotides are numbered in 3'-to-5' direction from the 3' terminus of genome RNA in both cases. Horizontal dashed lines indicate the chosen boundaries for the top and bottom portions of the respective 3'SLs, based on previous studies (Blackwell, J. and M. A. Brinton 1996 *J Virol* 69:5650-5658; Blackwell, J. L. and M. A. Brinton 1997 *J Virol* 71:6433-6444; Zeng, L. et al. 1998 *J Virol* 72:7510-7522). Dotted lines between nucleotides of the respective small stem and loop structures and the long stems of both 3'SLs indicate putative pseudoknot structures (Shi, P.-Y. et al. 1996 *Biochemistry* 35:4222-4230). An 11-base-pair (bp) segment of the long stem in the DEN2 3'SL that was required for replication of mutant DEN2 virus RNAs containing DEN/WN virus chimeric 3'SL nucleotide sequences (dengue-required sequence, DRS) is shown in boldface and underlined (Zeng, L. et al. 1998 *J Virol* 72:7510-7522). Nucleotides comprising the putative major binding site for the TEF, eF1α, in the WN virus 3'SL, nt 64 to 61 (Blackwell, J. L. and M. A. Brinton 1997 *J Virol* 71:6433-6444) are circled. The 5-bp segment in the top part of the long stem in the WN virus 3'SL representing the TEF-binding domain is shown in boldface and underlined. Nucleotides U4-U76 which form a bulge in the bottom portion of the long stem of the DEN2 3'SL are circled. The loci of relevant bulges in the DRS (bulges 1 and 2) and the U4-U76 bulges in the DEN2 3'SL and the TEF-binding domain in the WN virus 3'SL are indicated by adjacent horizontal arrows. Arrowheads indicate nt numbers in the 3'-to-5' direction.

FIG. 3. (A) Nucleotide sequences of mutant 3'SLs in WNmutC1 (SEQ ID NO: 3), -A1 (SEQ ID NO: 4), and -A1L (SEQ ID NO: 5) RNAs, excluding that of the small stem and loop defined by wt WN virus nt 80 to 95 (FIG. 1) are shown. Nucleotides native to the DEN2 3'SL are shown in roman type. Nucleotides native to the wt WN virus 3'SL are shown in boldface. Horizontal dashed lines indicate the boundaries between WN virus and DEN2 nucleotide sequences, as labeled. The 5-bp TEF-binding domain in C1 RNA is indicated by brackets and an asterisk. (+), mutant RNA replicated efficiently after transfection of BHK (and Vero) cells, in that cells were 100% positive by IFA within 5 days post-transfection (see FIG. 2). (−), transfected cells remained negative by IFA for 20 days post-transfection. (B) The nucleotide sequence of the long stem and loop at the 3' terminus of the WNmutC1 RNA (SEQ ID NO: 6) transcribed from C1 mutant DNA and used to transfect cells is shown on the left (input). Spontaneous mutations of the C1 long stem and loop in genomes of replicating C1 virus are shown on the right (virion RNAs). The TEF-binding domain in C1 RNA is bracketed and marked by an asterisk. Boldface type indicates the WN 3'SL nucleotides. Roman type indicates DEN2 3'SL nucleotides. The horizontal dashed lines indicate the boundary between the top (t) and bottom (b) of the wt WN virus 3'SL (FIG. 1), which also constitutes the boundary between DEN2 (DEN) and WN virus nucleotide sequences in the C1 3'SL. The 3'SL in recovered C1 virus RNA was cloned, and six representative cloned DNAs were sequenced. *a (SEQ ID NO: 7), b (SEQ ID NO: 8), and c (SEQ ID NO: 9) indicate, respectively, each of the three spontaneous mutations of the C1 3'SL detected in C1 virion RNAs by this method. Top portions of the nucleotide sequences of C1 3'SL variants detected in replicating virus that did not deviate from that of input C1 RNA are indicated by the heavy vertical dashed lines. Nucleotides inserted or substituted into the C1 3'SL by spontaneous mutation are enclosed by a box or rectangle. Nucleotides spontaneously deleted from the C1 3'SL are enclosed in an oval. , ratios of the respective mutant C1 nucleotide sequences in a total of six DNAs sequenced are indicated by fractions.

FIG. 6. The nucleotide sequence of the long stem-loop structure of the WNmutE 3'SL is depicted (SEQ ID NO: 17). Boldface type, nucleotides native to the wt WN virus 3'SL. Roman type, nucleotides native to the wt DEN2 3'SL. Horizontal dashed lines labeled WN and DEN indicate where a ds segment comprising wt WN virus nt 14 to 20 and 61 to 66, including the TEF-binding domain, was deleted and DEN2 nt 12 to 19 and 61 to 67 were inserted (FIG. 1). The inserted DEN2-specific nucleotides formed the major part of a ds segment shown in a previous study (Zeng, L. et al. 1998 *J Virol* 72:7510-7522) to be required for replication of DEN2 RNAs containing chimeric DEN2/WN virus 3'SLs, and they are underlined.

FIG. 8. The nucleotide sequence of the long stem-loop structure in the WNmutF1 3'SL is depicted (SEQ ID NO: 18). Boldface type indicates nucleotides native to the wt 3'SL. Roman type indicates nucleotides native to the wt DEN2 3'SL. The horizontal dashed line indicates the boundary between DEN2 and WN virus 3'SL nucleotide sequences. The TEF-binding domain is indicated by brackets and an asterisk adjacent to the left-hand strand of the segment. Nucleotides forming the U-U bulge created in the WN sequence by substituting DEN2 nucleotides for WN virus nucleotides that comprise the lowermost 7 bp of the respective long stems (FIG. 1) are circled. (+), Mutant RNA replicated efficiently after transfection of BHK (and Vero) cells compared to wt RNA.

DETAILED DESCRIPTION OF THE PREFERRED EMBODIMENT

Figure 2:
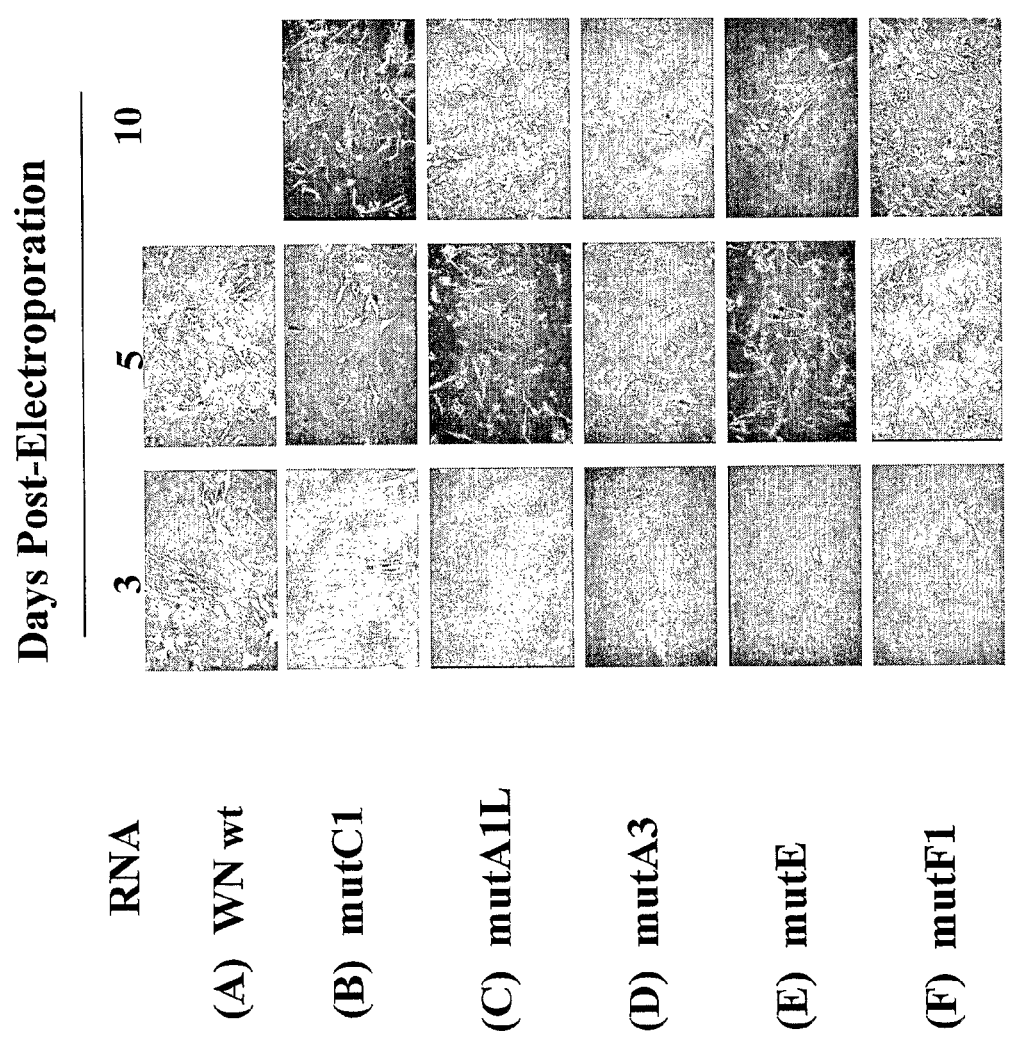
FIG. 2. Indirect IFAs after transfection of mutant WN virus RNAs. RNAs were derived by transfection of wt and mutant WN virus genome-length DNAs and used to transfect hamster kidney cells (BHK-21). On the days indicated, cells were replated on a chamber slide, and IFA was performed by standard methods with a polyclonal mouse anti-WN virus hyperimmune ascitic fluid on the days indicated. The nucleotide sequences of the 3'SLs in mutant C1, A1L, A3, E, and F1 RNAs are shown in FIGS. 3A, 5, 6, and 8.

All flavivirus genomes contain a 3' terminal stem-loop secondary structure (3'SL) formed by the most downstream approximately 100 nucleotides of the viral RNA. The 3'SL is required for virus replication and has been shown to bind both virus-coded and cellular proteins. Results of the present study using an infectious DNA for WN virus strain 956 initially demonstrated that the dengue virus serotype 2 (DEN2) 3'SL nucleotide sequence could not substitute for that of the WN 3'SL to support WN genome replication. To determine what WN-specific 3'SL nucleotide sequences were required for WN replication, WN 3'SL nucleotide sequences were selectively deleted and replaced by analogous segments of the DEN2 3'SL nucleotide sequence such that the overall 3'SL secondary structure was not disrupted. Top and bottom portions of the WN 3'SL were defined according to previous studies (Blackwell, J. L. and Brinton, M. A. 1997 *J Virol* 71:6433-6444; Zeng, L. et al. 1998 *J Virol* 72:7510-7522). A bulge in the top portion of the long stem of the WN 3'SL was essential for replication of mutant WN RNAs, and replication-defective RNAs failed to produce negative strands in transfected cells. Introduction of a second bulge into the bottom portion of the long stem of the wild type WN 3'SL markedly enhanced the replication competence of WN virus in mosquito cells but had no effect on replication in mammalian cells. This second bulge was identified as a host-cell specific enhancer of flavivirus replication. Results indicated that bulges and their topological location within the long stem of the 3'SL are primary determinants of replication competence for flavivirus genomes.

WN Viruses and Chimeric WN Viruses Having One or More Mutations That Result in Decreased Neurovirulence, Methods of Making Such WN Viruses, and Methods for Using These WN Viruses to Prevent or Treat WN Virus Infection The invention provides WN viruses and chimeric WN viruses having one or more mutations that result in decreased neurovirulence, methods of making such WN viruses, and methods for using these WN viruses to prevent or treat WN virus infection. Neurovirulence is the propensity of WN virus to infect nervous tissue of the host after invasion of the central nervous system (CNS). WN virus infection of the CNS can result in inflammation and injury of the brain and spinal cord (i.e., encephalitis), impaired consciousness, paralysis, and convulsions. The mutation (or mutations) in the WN virus of the invention is present in the 3' terminal stem loop secondary structure (3'SL) formed by the most downstream approximately 100 nucleotides of the viral RNA, which we have shown plays a role in determining attenuation. The viruses and methods of the invention are described further, as follows.

One example of a WN virus that can be used in the invention is WN virus strain 956. The applicability of the invention to all members of the WN virus taxonomic group is inferred by the observation that the properties of other WN virus strains are similar to that of any one WN virus strain. (Brinton, M. A. 2002 *Ann Rev Microbiol* 56:371-402.) WN viruses have been grouped into two genetic lineages (1 and 2) on the basis of signature amino acid substitutions or deletions in their envelope proteins. All the WN virus isolates associated thus far with outbreaks of human disease have been in linage 1. Lineage 2 viruses are restricted to endemic enzootic infections in Africa.

Mutations can be made in the 3'SL of a wild type infectious clone, e.g., WN virus strain 956 or an infectious clone of another wild type, virulent WN virus, and the mutants can then be tested in an animal model system (e.g., in mouse and/or monkey model systems) to identify sites affecting neurovirulence. Reduction in neurovirulence is judged by, for example, detection of decreased viremia and/or brain injury in the model system (see below for additional details). One or more additional mutations found to decrease neurovirulence of the wild-type virus are optionally introduced into a wild type WN virus, and these mutants are tested in an animal model system (e.g., in a mouse and/or a monkey model system) to determine whether the resulting mutants have decreased neurovirulence. Mutants that are found to have decreased neurovirulence can then be used as new vaccine strains that have increased safety, due to decreased levels of neurovirulence.

In addition to the viruses listed above, WN viruses including chimeric WN viruses that include one or more mutations that decrease neurovirulence are included in the invention. These chimeras can consist of a flavivirus (i.e., a backbone flavivirus) in which a structural protein (or proteins) has been replaced with a corresponding structural protein (or proteins) of a second virus (i.e., WN virus). For example, the chimeras can consist of a backbone flavivirus in which the prM and E proteins of the flavivirus have been replaced with the prM and E proteins of the second virus (i.e., WN virus). The chimeric viruses can be made from any combination of viruses. The WN virus against which immunity is sought is the source of the inserted structural protein(s).

As is noted above, mutations that are included in the viruses of the present invention decrease neurovirulence. These mutations are present in the WN 3'SL structure to limit the neurovirulence of the virus. Mutations can be made in the 3'SL using standard methods, such as site-directed mutagenesis. One example of the type of mutation present in the viruses of the invention is substitutions, but other types of mutations, such as deletions and insertions, can be used as well. In addition, as is noted above, the mutations can be present singly or in the context of one or more additional mutations.

In one embodiment of the present invention nucleic acid substitutions are made to the 3'SL structure of the WN virus to limit the replicative ability of the virus in cultured host cells. The nucleotide sequences of the WN 3'SL are substituted for analogous nucleotide segments of DEN1, DEN2, DEN3 or DEN4 3'SL, resulting in a series of WN/DEN hybrid 3'SLs. In one embodiment, the entire 3'SL structure of the WN virus corresponding to about bases 1 to 95 may be substituted with a suitable nucleic acid source. In another embodiment, the top portion of the 3'SL structure of the WN virus corresponding to about bases 16 to 65 may be substituted with a suitable replacement sequence. In another embodiment, the bottom portion of the 3'SL structure of the WN virus corresponding to about bases 1 to 15 and 66 to 95 may be substituted. In another embodiment, the bottom halve of the long stem portion of the 3'SL structure of the WN virus corresponding to about bases 1-15 and 66-79 may be substituted. In still another embodiment, the small stem and loop portion of the 3'SL structure of the WN virus corresponding to about bases 80-95 may be substituted. In yet another embodiment, the upper-most portion of the bottom half of the long stem portion of the 3'SL structure of the WN virus corresponding to about bases 8-15 and 66-72 may be substituted. In again another embodiment, the lower-most portion of the bottom half of the long stem portion of the 3'SL structure of the WN virus corresponding to about bases 1-7 and 73-79 may be substituted. In yet another embodiment, the double-loop structure atop the long stem of the 3'SL structure of the WN virus corresponding to about bases 29 to 52 (containing the flavivirus-conserved pentanucleotide sequence 5'CACAG3') may be substituted. In still another embodiment, the TEF-binding domain of the 3'SL structure of the WN virus corresponding to about bases 14-20 and 61-66 may be substituted.

The viruses (including chimeras) of the present invention can be made using standard methods in the art. For example, an RNA molecule corresponding to the genome of a virus can be introduced into host cells, e.g., Vero cells, from which (or the supernatants of which) progeny virus can then be purified. In this method, a nucleic acid molecule (e.g., an RNA molecule) corresponding to the genome of a virus is introduced into the host cells, virus is harvested from the medium in which the cells have been cultured, and the virus is formulated for the purposes of vaccination.

The viruses of the invention can be administered as primary prophylactic agents in adults or children at risk of infection, or can be used as secondary agents for treating infected patients. For example, in the case of WN virus and WN virus chimeras, the vaccines can be used in adults or children at risk of WN virus infection, or can be used as secondary agents for treating WN virus-infected patients. Examples of patients who can be treated using the WN virus-related vaccines and methods of the invention include (i) children in areas in which WN virus is endemic, (ii) foreign travelers, (iii) military personnel, and (iv) patients in areas of a WN virus epidemic. Moreover, inhabitants of regions into which the disease has been observed to be expanding (e.g., the United States), or regions in which it may be observed to expand in the future can be treated according to the invention.

The viruses of the invention can also be administered as primary prophylactic agents in other mammals and avians, particularly equidae, such as horses, donkeys, asses, etc., at risk of infection, or can be used as secondary agents for treating infected animals.

Formulation of the viruses of the invention can be carried out using methods that are standard in the art. Numerous pharmaceutically acceptable solutions for use in vaccine preparation are well known and can readily be adapted for use in the present invention by those of skill in this art (see, e.g., Remington's Pharmaceutical Sciences (18th edition), ed. A. Gennaro, 1990, Mack Publishing Co., Easton, Pa.). The viruses can be diluted in a physiologically acceptable solution, such as sterile saline or sterile buffered saline. In another example, the viruses can be administered and formulated, for example, as a fluid harvested from cell cultures infected with WN virus or chimeric WN virus.

The vaccines of the invention can be administered using methods that are well known in the art, and appropriate amounts of the vaccines administered can be readily be determined by those of skill in the art. For example, the viruses of the invention can be formulated as sterile aqueous solutions containing between $10^2$ and $10^7$ infectious units (e.g., plaque-forming units or tissue culture infectious doses) in a dose volume of 0.1 to 1.0 ml, to be administered by, for example, intramuscular, subcutaneous, or intradermal routes. Further, the vaccines of the invention can be administered in a single dose or, optionally, administration can involve the use of a priming dose followed by a booster dose that is administered, e.g., 2-6 months later, as determined to be appropriate by those of skill in the art.

Optionally, adjuvants that are known to those skilled in the art can be used in the administration of the viruses of the invention. Adjuvants that can be used to enhance the immunogenicity of the viruses include, for example, liposomal formulations, synthetic adjuvants, such as (e.g., QS21), muramyl dipeptide, monophosphoryl lipid A, or polyphosphazine. Although these adjuvants are typically used to enhance immune responses to inactivated vaccines, they can also be used with live vaccines. In addition, genes encoding cytokines that have adjuvant activities can be inserted into the viruses. Thus, genes encoding cytokines, such as GM-CSF, IL-2, IL-12, IL-13, or IL-15, can be inserted together with foreign antigen genes to produce a vaccine that results in enhanced immune responses, or to modulate immunity directed more specifically towards cellular or humoral responses.

Nucleic acid sequences of WN viruses and dengue viruses are useful for designing nucleic acid probes and primers for the detection of chimeric 3'SLs in a sample or specimen with high sensitivity and specificity. Probes or primers corresponding to chimeric 3'SLs can be used to detect the presence of chimeric 3'SLs in general in the sample, to quantify the amount of chimeric 3'SLs in the sample, or to monitor the progress of therapies used to treat WN virus infection. The nucleic acid and corresponding amino acid sequences are useful as laboratory tools to study the organisms and diseases and to develop therapies and treatments for the diseases.

Nucleic acid probes and primers selectively hybridize with nucleic acid molecules encoding chimeric 3'SLs or complementary sequences thereof. By "selective" or "selectively" is meant a sequence which does not hybridize with other nucleic acids to prevent adequate detection of the chimeric 3'SLs. Therefore, in the design of hybridizing nucleic acids, selectivity will depend upon the other components present in the sample. The hybridizing nucleic acid should have at least 70% complementarity with the segment of the nucleic acid to which it hybridizes. As used herein to describe nucleic acids, the term "selectively hybridizes" excludes the occasional randomly hybridizing nucleic acids, and thus has the same meaning as "specifically hybridizing." The selectively hybridizing nucleic acid probes and primers of this invention can have at least 70%, 80%, 85%, 90%, 95%, 97%, 98% and 99% complementarity with the segment of the sequence to which it hybridizes, preferably 85% or more.

The present invention also contemplates sequences, probes and primers that selectively hybridize to the encoding nucleic acid or the complementary, or opposite, strand of the nucleic acid. Specific hybridization with nucleic acid can occur with minor modifications or substitutions in the nucleic acid, so long as functional species-species hybridization capability is maintained. By "probe" or "primer" is meant nucleic acid sequences that can be used as probes or primers for selective hybridization with complementary nucleic acid sequences for their detection or amplification, which probes or primers can vary in length from about 5 to 100 nucleotides, or preferably from about 10 to 50 nucleotides, or most preferably about 18-24 nucleotides. Isolated nucleic acids are provided herein that selectively hybridize with the species-specific nucleic acids under stringent conditions and should have at least five nucleotides complementary to the sequence of interest as described in *Molecular Cloning: A Laboratory Manual*, 2$^{nd}$ ed., Sambrook, Fritsch and Maniatis, Cold Spring Harbor Laboratory, Cold Spring Harbor, N.Y., 1989.

If used as primers, the composition preferably includes at least two nucleic acid molecules which hybridize to different regions of the target molecule so as to amplify a desired region. Depending on the length of the probe or primer, the target region can range between 70% complementary bases and full complementarity and still hybridize under stringent conditions. For example, for the purpose of detecting the presence of chimeric 3'SLs, the degree of complementarity between the hybridizing nucleic acid (probe or primer) and the sequence to which it hybridizes is at least enough to distinguish hybridization with a nucleic acid from other organisms.

The nucleic acid sequences of the invention include a diagnostic probe that serves to report the detection of a cDNA amplicon amplified from the viral genomic RNA template by using a reverse-transcription/polymerase chain reaction (RT-PCR), as well as forward and reverse amplimers that are designed to amplify the cDNA amplicon. In certain instances, one of the amplimers is designed to contain a vaccine virus-specific mutation at the 3'-terminal end of the amplimer, which effectively males the test even more specific for the vaccine strain because extension of the primer at the target site, and consequently amplification, will occur only if the viral RNA template contains that specific mutation.

Automated PCR-based nucleic acid sequence detection systems have been recently developed. TaqMan assay (Applied Biosystems) is widely used. A more recently developed strategy for diagnostic genetic testing makes use of molecular beacons (Tyagi and Kramer 1996 *Nature Biotechnology* 14:303-308). Molecular beacon assays employ quencher and reporter dyes that differ from those used in the TaqMan assay. These and other detection systems may used by one skilled in the art.

Figure 1:
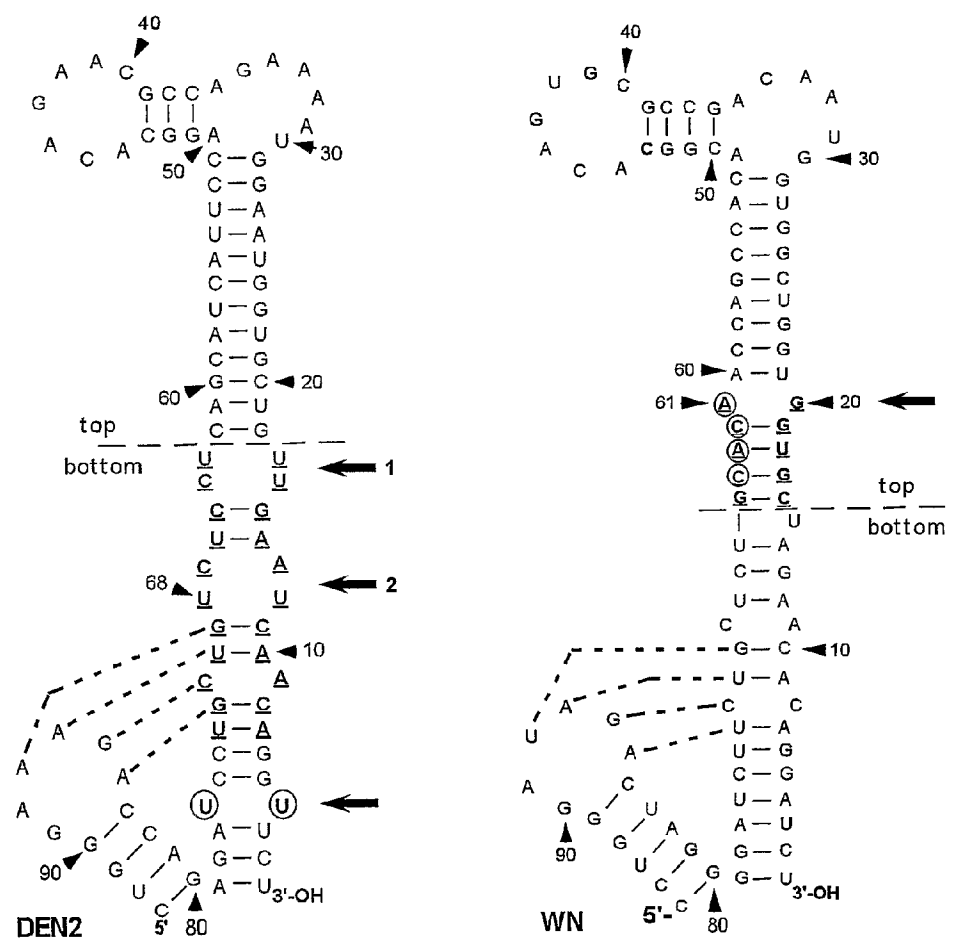

The Topology of Bulges in the Long Stem of the Flavivirus 3' SL Is a Major Determinant of RNA Replication Competence Phenotype of WN/D2-SL RNA DEN2 and WN viruses are members of different groups among mosquito-borne flaviviruses, based on serologic and genetic relatedness (Calisher, C. H. et al. 1989 *J Gen Virol* 70:37-43). The nucleotide sequences of the 3'SL for the genome of WN virus strain 956 (Yamshchikov, V. F. et al. 2001 *Virology* 281:294-304) and that for DEN2 strain New Guinea C (NGC) (Zeng, L. et al. 1998 *J Virol* 72:7510-7522) are shown in FIG. 1. Computer analysis revealed that there was about 65% similarity between these two sequences. In a previous study of DEN2 virus replication (Zeng, L. et al. 1998 *J Virol* 72:7510-7522), in which DEN2 genome RNAs containing DEN2/WN chimeric 3'SL nucleotide sequences were assessed for replication competence, results showed that an 11-bp segment, comprising the top-most part of the bottom portion of the long stem in the DEN2 3'SL nucleotide sequence (FIG. 1), the dengue-required sequence [DRS], was essential for replication of DEN2 virus. Here, we conducted the converse investigation to determine the minimal requirement for WN virus 3'SL-specific nucleotide sequences for replication of WN virus mutant RNAs containing WN/DEN2 chimeric 3'SLs. The wt WN virus strain 956 infectious DNA used as the basis for constructing all mutant viruses described in this study was reported previously (Yamshchikov, V. F. et al. 2001 *Virology* 281:294-304).

Replication of wt and mutant RNAs was assessed by an immune fluorescence assay (IFA) for WN virus antigens in transfected cells, with murine polyclonal anti-WN antibodies on days 3, 5, 10, 15, and 20 postelectroporation. All but one mutant RNA exhibited one of two distinctly different phenotypes in the IFA. Viable mutant RNAs gave positive results by IFA within 5 days after transfection and 100% WN virus antigen-positive cells at or prior to the 10-day time point after transfection. Mutant RNAs that gave negative results by IFA after 20 days of observation were said to display a lethal phenotype.

We initially created a cloned mutant WN virus DNA (WN/D2-SL) representing the wt WN virus strain 956 genome sequence, except that the last 95 nucleotide of the WN virus genome (representing the entire WN virus 3'SL) was replaced by the 3'-terminal 93 nucleotide of the wt DEN2 sequence (representing the entire DEN2 3'SL [FIG. 1]). RNAs derived from transcription of WN/D2-SL mutant and WN virus wt DNAs were electroporated into both Vero and BHK cells. (Both wt parent viruses, DEN2 NGC and WN virus strain 956, replicate vigorously in either cell line.) For mutant WN/D2-SL RNA, no WN virus-specific antigens were detected in transfected cells for the entire duration of this experiment; it therefore displayed the lethal phenotype. In contrast, WN virus wt RNA-transfected cells were positive for WN virus antigens by IFA after 24 hr, and nearly 100% of cells in the monolayer were positive by day 5 (FIG. 2A). The replication phenotypes of all wt and mutant RNAs were essentially identical after transfection of either BHK or Vero cells. Therefore, only the results of the IFA on BHK cells are shown.

To exclude the possibility that the lethal phenotype of WN/D2-SL RNA was due to an occult mutation upstream from the 3'SL in WN/D2-SL DNA, we first generated a revertant wt WN virus DNA from WN/D2-SL DNA, by substituting a fragment containing the 3'-terminal 1.1 kb of the wt WN DNA (spanning the WN nucleotide sequence between a unique BclI restriction site at nucleotide 9833 and the 3'-terminal XbaI restriction site at nucleotide 10962) for the analogous mutant fragment in the WN/D2-SL DNA. RNA transcribed from this rescued WN/D2-SL DNA was infectious, and the resulting virus exhibited growth kinetics analogous to that of the parental WN virus. This indicated that WN/D2-SL DNA did not contain an occult lethal mutation upstream from the BclI site and that the PCR-synthesized wt 1.1 kb BclI/XbaI fragment was able to support virus replication.

We also recreated the wt WN and WN/D2-SL DNAs as full-length PCR products and demonstrated that wt RNA transcribed from the PCR template was infectious while WN/D2-SL RNA derived in the same manner was not. This additionally confirmed that the failure of WN/D2-SL RNA to replicate was due to the substitution of the DEN2 3'SL nucleotide sequence for that of the WN virus 3'SL, despite the similarity between the two 3'SLs in secondary structure (FIG. 1).

Nucleotide Sequence Elements of the WN Virus 3'SL Required for WN Virus Replication We next sought to determine what portions of the wt WN-specific 3'SL nucleotide sequence were required to restore efficient WN virus replication. To perturb the nucleotide sequence of the 3'SL without altering its predicted stem-loop structure, portions of the 3' terminal 79 nucleotides of the DEN2 3'SL sequence were substituted for analogous segments of the 3' terminal 79 nucleotides of the WN virus 3'SL sequence (FIG. 1), in the context of the WN virus infectious DNA. Substitution mutations did not extend into the small stein and loop structure formed by WN virus nucleotides 79 to 95, because the WN virus and DEN2 sequences in this region were shown to be freely exchangeable in the previous study centered on DEN2 virus replication (Zeng, L. et al. 1998 *J Virol* 72:7510-7522). We defined the top and bottom of the WN virus and DEN2 3'SL in accordance with previous studies (Blackwell, J. and M. A. Brinton 1996 *J Virol* 69:5650-5658; Blackwell, J. L. and M. A. Brinton 1997 *J Virol* 71:6433-6444; Zeng, L. et al. 1998 *J Virol* 72:7510-7522). Computer analyses (Matzura, O. and A. Wennborg 1996 *Computer Applications in the Biosciences [CABIOS]* 12:247-249) of all resulting chimeric WN/DEN2 3'SL nucleotide sequences indicated that each would form the stem-loop structures shown in FIGS. 3-8.

Figure 3A:
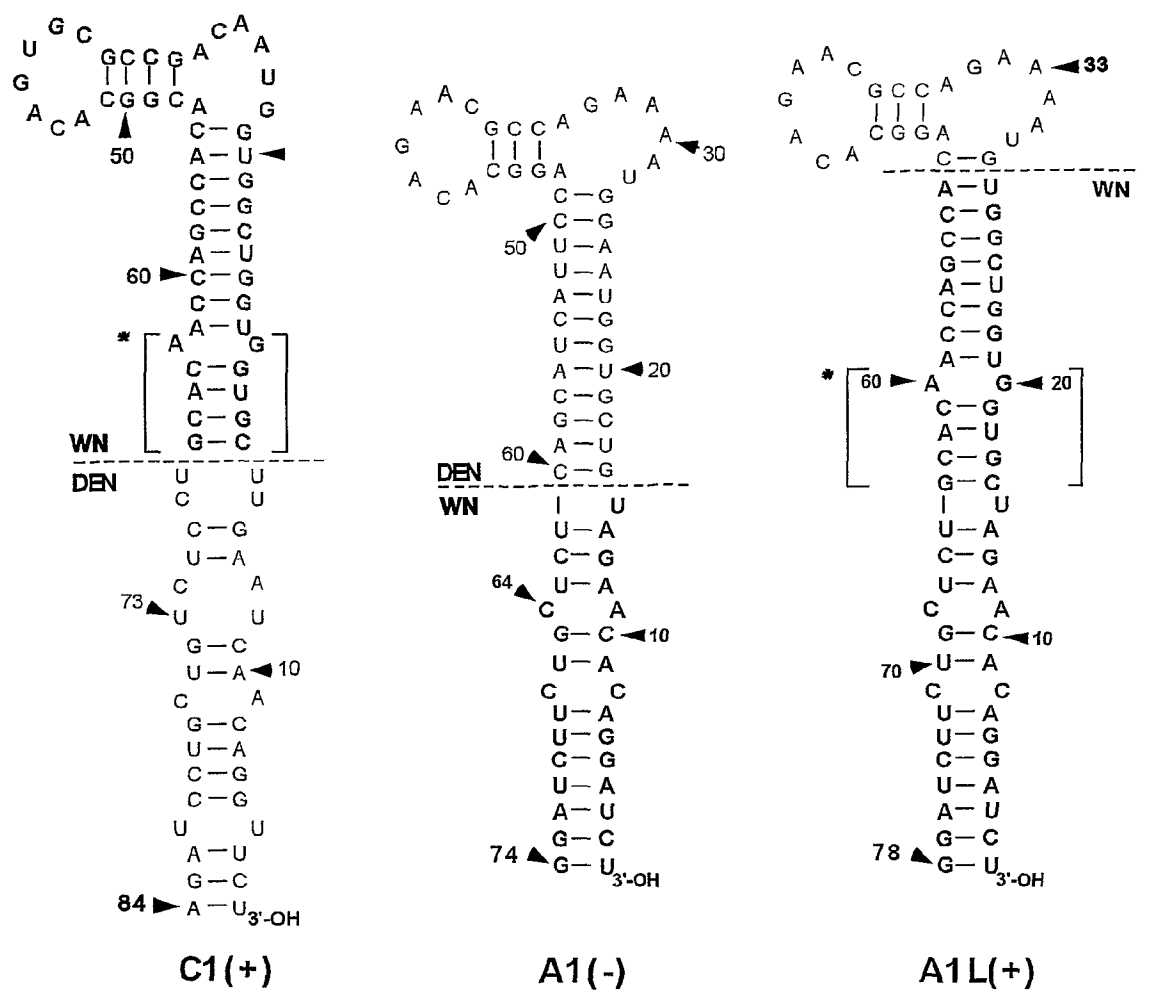

Initially, two mutant WN virus DNAs containing chimeric WN/DEN2 3'SL nucleotide sequences were cloned (FIG. 3A). WNmutA1 DNA contained a substitution of the top half of the WN virus 3'SL long stem (nt 16 to 65, numbering in the upstream direction from the 3'-terminal nucleotide of the genome [FIG. 1]) by the analogous segment of the DEN2 3'SL (nt 18 to 62). WNmutC1 DNA contained the converse substitution; the bottom half of the WN virus long stem-and-loop structure sequence, nucleotides 1 to 15 and 66 to 79, was replaced by DEN2 nucleotides 1 to 17 and 63 to 79, respectively. RNAs derived from WNmutA1 and WNmutC1 DNAs were transfected into BHK or Vero cells in separate experiments. For WNmutA1 RNA, IFA was negative up to day 20 post-transfection, whereas for WNmutC1 RNA, 40 to 60% of cells were positive by day 5 after transfection, and 100% were positive by day 10, as shown for BHK cells (FIG. 2B). As a positive control, wt WN virus RNA-transfected cells were 100% positive by IFA within 5 days post-transfection in the same experiment. Thus, substitution of the top half of the WN virus 3'SL by the nucleotide sequence of the top half of the DEN2 3'SL was lethal, whereas substitution of the bottom half of the long stem in the WN virus 3'SL nucleotide sequence with the analogous DEN2 3'SL nucleotide sequences was well tolerated and gave rise to a viable mutant virus.

The 3'termini of genomic RNAs derived from WNmutC1 virus and that of all other viable mutant viruses were sequenced to determine whether spontaneous mutations had occurred within the 3'SL after transfection. For WNmutC1 RNA, results showed that there were heterogeneities at certain nucleotide positions in the 3'SL. (We assayed for heterogeneity of the average nucleotide sequence by a visual search for peaks coexisting at a single site on the computer-generated graph of the nucleotide sequence that constitutes the output of the automated sequencers; see Example 1. We could detect heterogeneity at a given site in the nucleotide sequence at the level of one substitution mutation per 5 to 10 molecules by this method.) Therefore, PCR products representing the C1 3'SL in C1 virus RNA were cloned, and six cloned DNA fragments were sequenced. All six DNAs contained spontaneous mutations of the bottom portion of the long stem in the C1 3'SL (FIG. 3B; sequences a to c, but all spontaneous mutations conserved the general predicted secondary structure of the C1 3'SL. Sequence b was detected in three of six clones, and after three additional passages of WNmutC1 virus in Vero cells, sequence b was dominant in C1 genome RNAs. In the C1b 3'SL, an A was inserted between U at position 3 (U3) and U4, and a U was inserted between U81 and A82 of the predicted C1 nucleotide sequence. The G6-C81 base pair was deleted. These mutations had the net effect of shifting the U4-U81 bulge in the predicted C1 3'SL upward by one (U/A) base pair from the bottom of the long stem. The apparent deletion of one or two 3' terminal nucleotides from C1 spontaneous mutants a and c could have been an artifact due to the activity of enzymes used to circularize viral RNA prior to PCR. The occurrence of second-site mutations in the C1 3'SL was unique for viable genomes containing WN/DEN2 chimeric 3'SLs; in all other cases the respective mutant 3'SL nucleotide sequences were stable in replicating viral genomes.

We next generated WNmutA1L DNA as a full-length PCR product, using wt WN DNA as template and a 3' negative-sense primer encoding the A1L mutations, to identify more specifically the nucleotides in the top half of the WN virus 3'SL that were required for WN virus replication. In A1L DNA, only the double-loop structure atop the long stem (WN nucleotides 29 to 52) (FIGS. 1 and 3A) was replaced by the analogous nucleotide sequence of the DEN2 3'SL. WNmutA1L RNA was infectious in both BHK and Vero cell monolayers. About 50% of cells in either transfected monolayer were positive for WN virus antigens by day 5 after transfection, and cells were 100% positive by day 10, as shown for BHK cells (FIG. 2C). This result indicated that the lethal phenotype of WNmutA1 RNA was due to the absence in that construct of the 14-bp top portion of the long stem in the wt WN virus 3'SL.

This finding was not consistent with the previously mentioned study (Zeng, L. et al. 1998 *J Virol* 72:7510-7522), in which part of the bottom portion of the DEN2 3'SL nucleotide sequence was shown to be required for replication of DEN2 RNAs containing chimeric 3'SLs (FIG. 1). One possible explanation for the disparate results was that bulges in the top and bottom halves of the WN virus and DEN2 long stems, respectively, were required for replication of both virus species. The lower portion of the top half of the long stem in the WN virus 3'SL contained a bulge formed by the apposition of non-complementary nucleotides G20 and A61, whereas no analogous bulge occurs in the top half of the DEN2 3'SL. Conversely, the dengue-required segment DRS contained two bulges that were not precisely represented in the analogous region of the WN virus 3'SL. We therefore focused further attention on a 5-bp double-stranded (ds) segment (WN virus nucleotides 16 to 20 and 61 to 65) (FIG. 1) that included both the bulge formed by nt A61 and G20 and the major in vitro eF1-α binding site (Blackwell, J. L. and M. A. Brinton 1997 *J Virol* 71:6433-6444) in the WN virus long stem (the sequence 5'CACA3'; WN virus nucleotides 61-64) (FIG. 1). For the latter reason, we referred to the segment as the translation elongation factor (TEF)-binding domain.

Figure 4:
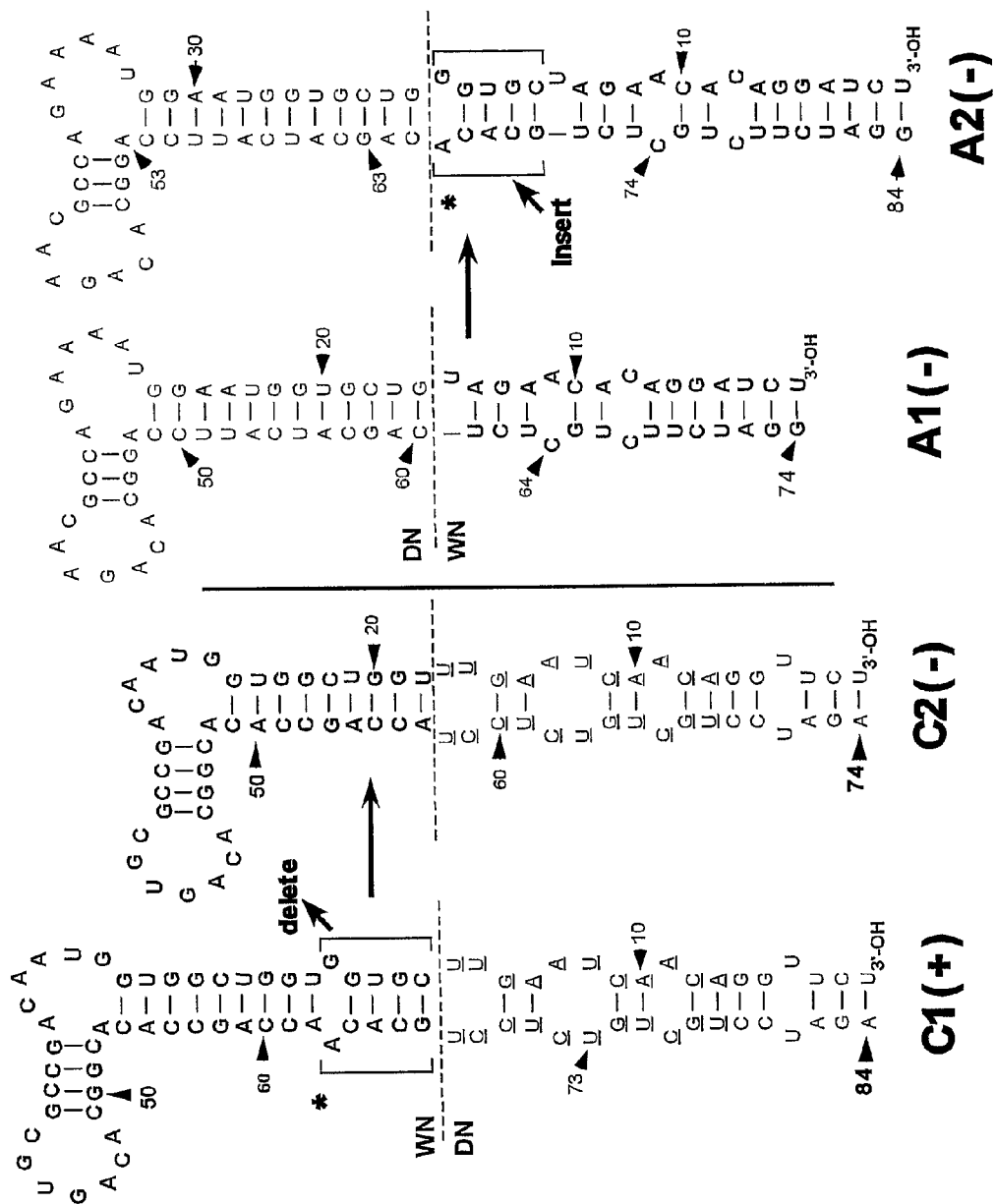
FIG. 4. Nucleotide sequences of the long stem-loop structures of 3'SLs present in WNmutC2 (A) (SEQ ID NO: 11) and WNmutA2 (B) (SEQ ID NO: 13) RNAs are depicted in comparison to WNmutC1 (SEQ ID NO: 10) and WNmutA1 (SEQ ID NO: 12) 3'SLs, respectively. Boldface type indicates nucleotides derived from the wt WN virus 3'SL sequence. Roman type, nucleotides derived from the wt DEN2 3'SL sequence. The 5-bp TEF-binding domain in C1 and A2 RNAs is indicated by brackets and an asterisk. Nucleotides included in the 11-bp ds segment previously shown to be required for DEN2 virus replication (Zeng, L. et al. 1998 *J Virol* 72:7510-7522) are underlined. Arrows indicate that the TEF-binding domain was deleted from the C1 3'SL to generate the C2 3'SL. Similarly, arrows indicate that the TEF-binding domain was inserted into the A1 3'SL where shown in order to generate the A2 3'SL. Dashed lines delineate both the boundary between top and bottom portions of the WN virus 3'SL and the boundary between WN and DEN2 (DN) nucleotide sequences. (+), mutant RNA replicated efficiently after transfection of BHK (and Vero) cells compared to wt RNA; (−), transfected cells remained negative by IFA for 20 days post-transfection.

To demonstrate a requirement for the TEF-binding domain in WN virus replication, we next generated WNmutC2 and WNmutA2 DNA templates as cloned recombinant plasmids (FIG. 4). WNmutC2 DNA was identical in nucleotide sequence to WNmutC1 DNA, except the TEF-binding domain was deleted. Conversely, WNmutA2 DNA was derived from WNmutA1 DNA by the insertion of the TEF-binding domain into the WNmutA1 3'SL nucleotide sequence at the boundary between the bottom and top parts of the A1 3'SL.

Figure 5:
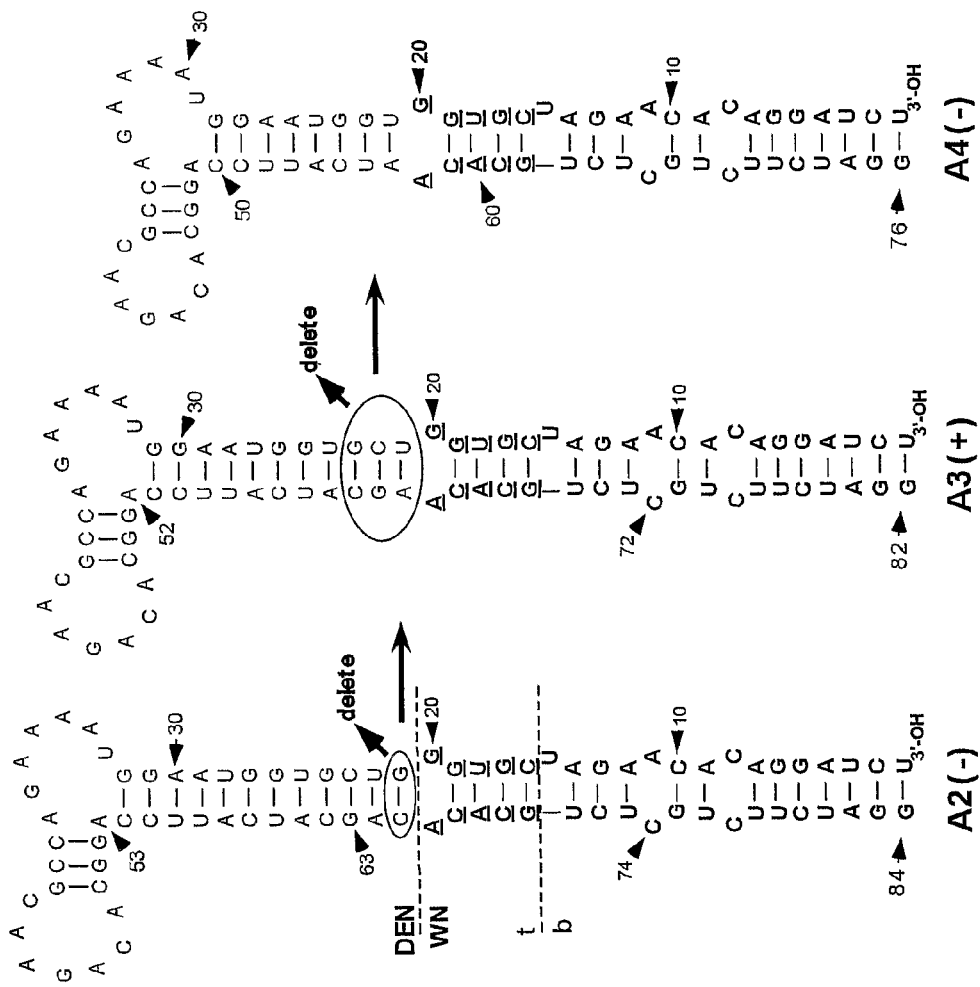
FIG. 5. Derivation of the 3'SLs in WNmutA3 (SEQ ID NO: 15) and WNmutA4 (SEQ ID NO: 16) RNAs from the A2 3'SL nucleotide sequence (SEQ ID NO: 14) is shown. Boldface type, nucleotides derived from the wt WN virus 3'SL nucleotide sequence. Roman type, nucleotides derived from the wt DEN2 3'SL nucleotide sequence. Arrows indicate that the G21-C65 base pair (enclosed by an oval) was deleted from the A2 3'SL to generate the A3 3'SL and that 3 bp (nt 21 to 23 and 61 to 63) (enclosed by an oval) were deleted from the A3 nucleotide sequence to generate the A4 3'SL nucleotide sequence. Horizontal dashed lines indicate, respectively, the boundary between DEN2 and WN virus nucleotide sequences in the context of the A2 3'SL and the top (t) and bottom (b) portions of the WN virus 3'SL, as defined in previous studies (Blackwell, J. and M. A. Brinton 1996 *J Virol* 69:5650-5658; Blackwell, J. L. and M. A. Brinton 1997 *J Virol* 71:6433-6444; Zeng, L. et al. 1998 *J Virol* 72:7510-7522). Nucleotides comprising the TEF-binding domain (see below) are underlined. (+), mutant RNA replicated efficiently after transfection of BHK (and Vero) cells compared to wt RNA; (−), transfected cells remained negative by IFA for 20 days posttransfection.
Figure 7:
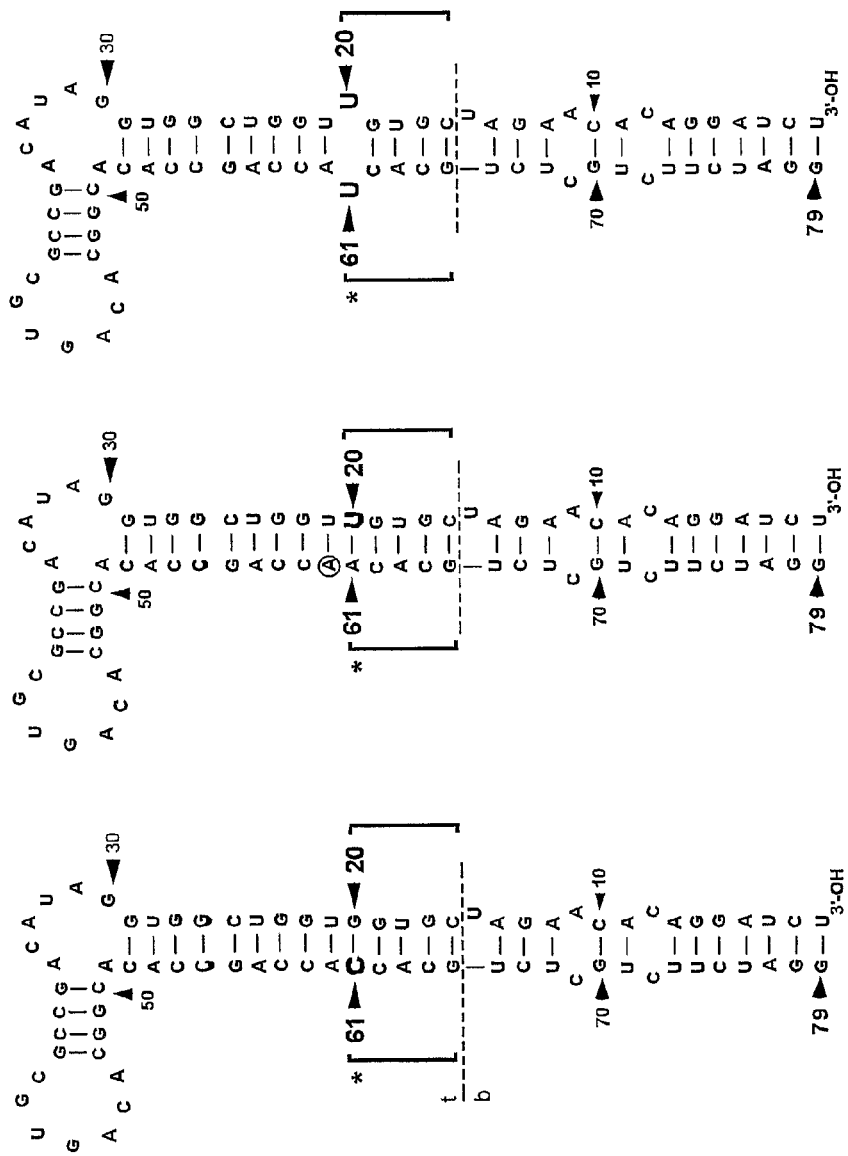
FIG. 7. Nucleotide sequences of the long stem and loop of 3'SLs present in A61C (SEQ ID NO: 19), G20U (SEQ ID NO: 20), and 2U (SEQ ID NO: 21) RNAs are depicted. A horizontal line indicates the boundary between the top (t) and bottom (b) portions of the wt WN virus 3'SL (Blackwell, J. and M. A. Brinton 1996 *J Virol* 69:5650-5658; Blackwell, J. L. and M. A. Brinton 1997 *J Virol* 71:6433-6444; Zeng, L. et al. 1998 *J Virol* 72:7510-7522). The TEF-binding domain in all three mutant nucleotide sequences is indicated by brackets and an asterisk to the left. For the A61C and G20U mutations, the loci of the substituted nucleotides are indicated in large, boldface type. For the 2U 3'SL, the U residues replacing A61 and G20, respectively, are shown in large boldface type. In the G20U nucleotide sequence, nucleotide A60, which spontaneously reverted to C in a portion of RNAs after transfection, is circled.

Neither WNmutC2 RNA nor WNmutA2 RNA was infectious in BHK or Vero cells. The phenotype of WNmutC2 RNA (lethal) compared to that of WNmutC1 RNA (viable) was consistent with a requirement for the TEF-binding domain for WN virus replication, but the lethal phenotype of WNmutA2 RNA was in conflict with that hypothesis. We postulated that failure of WNmutA2 RNA to replicate was related to the possibly excessive length of the long stem in the A2 3'SL (FIG. 4) and/or to the resulting perturbation of the spatial relationship of the bulge contained in the TEF-binding domain to other predicted bulge or loop structures within the 3'SL. Therefore WNmutA3 and WNmutA4 DNAs were generated as PCR products, as described for WNmutA1L (FIG. 5). WNmutA3 PCR-product DNA contained a deletion of a single DEN2-specific base pair (nucleotides G21 and C63) (FIGS. 1 and 5) at the lowermost boundary of the top of the WNmutA2 3'SL, and WNmutA4 PCR-product DNA contained a deletion of three additional DEN2-specific base pairs from the same region in the WNmutA1 3'SL (nts 21 to 24 and 62 to 65) (FIG. 5). WNmutA3 RNA exhibited a viable phenotype; 30% to 60% of cells were positive by IFA 3 to 5 days after transfection, and 100% of cells were positive at day 10 post-transfection (FIG. 2D). The A4 mutation was lethal for WN virus replication. The results for mutants WNmutC2 and WNmutA3 were consistent with the hypothesis that the WN virus-specific TEF-binding domain was necessary for the viability of mutant WN virus RNAs containing chimeric 3'SLs, but failure of WNmutA2 and -A4 RNAs to replicate indicated that there were additional constraints on the 3'SL secondary structure or nucleotide sequence that rendered these latter genomic RNAs nonviable. In addition, the results for WNmutA3 RNA demonstrated that WN nucleotides 21 to 29 and 52 to 60 (FIG. 1) were not necessary per se for WN genome replication.

Figure 6:
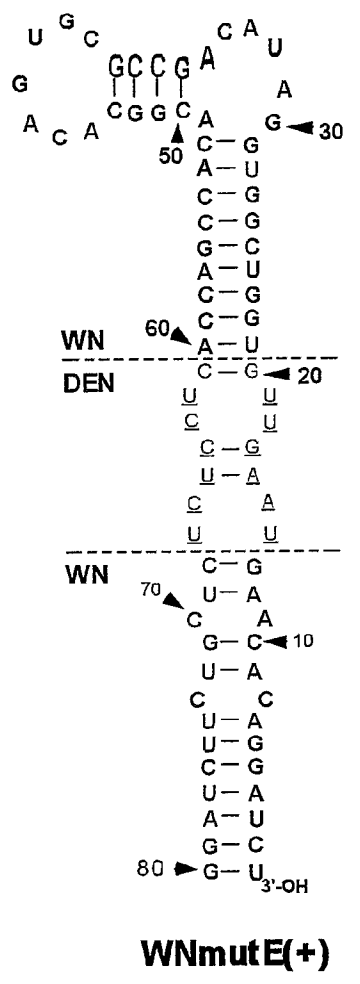

We next sought to determine whether the DRS (FIG. 1) (Zeng, L. et al. 1998 *J Virol* 72:7510-7522) could substitute for the TEF-binding domain, if it were inserted into the WN virus 3'SL in an analogous locus in the long stem. WNmutE DNA was cloned to address this question; it contained a substitution of DEN2 3'SL nucleotides 12 to 18 and 61 to 68 (FIG. 1) for nucleotides 14 to 20 and 61 to 66, respectively, of the wt WN virus 3'SL nucleotide sequence (FIG. 6). WNmutE RNA exhibited a viable phenotype that was nearly indistinguishable from that of wt WN RNA; 100% of cells in the transfected monolayers were positive by IFA within 5 days post-transfection (FIG. 2E). Thus, our question was answered in the affirmative. Since the TEF-binding domain and the substituted DEN2-specific ds segment of the DRS had little nucleotide sequence homology but both introduced a bulge into the top portion of the long stem of the WN 3'SL, this indicated that the bulge itself and its location within the long stem were a critical determinants of RNA replication competence independent of nucleotide sequence, at least in the context of mutant RNAs containing chimeric 3'SLs.

The Bulge in the TEF-Binding Domain

We constructed additional point-mutant WN virus DNAs as PCR products in order to determine whether the bulge in the TEF-binding domain was required for replication in the context of the wt WN virus 3'SL nucleotide sequence (FIG. 1). A61C (FIG. 7A) and G20U (FIG. 7B) RNAs were each predicted to lack the bulge in the TEF-binding domain, but in each mutant one of the two wt nucleotides that constituted the bulge was conserved. Both RNAs were infectious and gave viable virus with kinetics similar to those of wt WN virus RNA in our post-transfection IFA. However, nucleotide sequence analysis of RNAs derived from replicating viruses showed that all A61C mutant viral genomes had reverted, such that an A was present at position 61, and the wt A61-G20 bulge was restored. RNA from mutant G20U virus contained the expected substituted U at position 20 in the 3'SL (and therefore lacked the A61-G20 bulge) but was heterogeneous at nucleotide 60 in the wt WN virus 3'SL sequence (FIG. 7B). Therefore, the G20U virus was passaged one additional time in Vero cells, and five cloned DNAs representing the G20U 3'SL were sequenced. Results showed that a proportion (~1:5) of G20U viral genomes had sustained a novel nucleotide substitution mutation of A at position 60 to C (A60C), thus introducing a new potential bulge by apposition of mutant nucleotide C60 with wt nucleotide U21, displaced by one nucleotide pair compared to the A61-G20 bulge in the wt TEF-binding domain. After three additional passages of G20U mutant virus in Vero cells, the spontaneous A60C mutation and the deliberate G20U mutations had both reverted to wt in all molecules, restoring the wt A61-G20 bulge. These results collectively indicated that the bulge in the top portion of the long stem of the wt WN virus 3'SL was not dispensable.

To determine whether nucleotides A61 and/or G20 were per se required for WN virus replication, we generated the WNmut2U mutant DNA by PCR, in which both A61 and G20 were replaced by U (FIG. 7C). The 2U mutant 3'SL contained a bulge, created by the apposition of the substitution mutations, A61U and G20U. WNmut2U RNA replicated less efficiently than other viable mutant RNAs after transfection, in that transfected cells did not become 100% positive for WN virus antigens until day 15 after transfection. However, as a more certain indicator of its replication efficiency, WNmut2U virus recovered from transfected cells was used to infect Vero cells at a low MOI and reached a peak titer of $9 \times 10^6$ PFU/ml after 7 days. This peak titer was less than 10-fold different from that of wt WN virus in a similar assay at the same time point. Sequencing of the 3' terminus of the WNmut2U genome revealed that the 2U mutation was completely stable in RNA recovered from virus particles. These results indicated that nucleotides of A61 and G20 were not absolutely required for WN virus replication.

Introduction of a Bulge into the Bottom Part of the Long Stem of the WN Virus 3'SL One mutant DEN2 virus derived in the previous study of the DEN2 3'SL contained a substitution of the bottom 7 bp of the long stem in the DEN2 3'SL by the analogous 6 bp of the long stem of the WN virus 3'SL (Zeng, L. et al. 1998 *J Virol* 72:7510-7522). The resulting mutant DEN2mutF virus was host range restricted, in that it was severely retarded for replication in mosquito cells but replicated to wt titers in cultured monkey kidney cells. WNmutF1 DNA (FIG. 8) was constructed to determine whether the converse mutation could alter the host range of WN virus. It contained a replacement of the bottommost 7 bp of the long stem in the WN virus 3'SL (WN virus nucleotides 1 to 7 and 73 to 79) (FIG. 1) by the analogous 7 bp of the DEN2 3'SL (DEN2 nucleotides 1 to 7 and 73 to 79) (FIG. 1). This had the effect of introducing a "U-U" bulge into the bottom portion of the WN virus 3'SL long stem that was not present in the wt structure, formed by the apposition of U4 and U76 in the DEN2 nucleotide sequence. By IFA, WNmutF1 RNA had a viable phenotype nearly indistinguishable from that of the wt WN virus RNA after transfection of Vero or BHK cells (FIG. 2F). Data from growth curves indicated that WNmutF1 virus did have an altered host range in C6/36 cells (see below).

Specific Infectivity of Mutant RNA

Figure 3B:
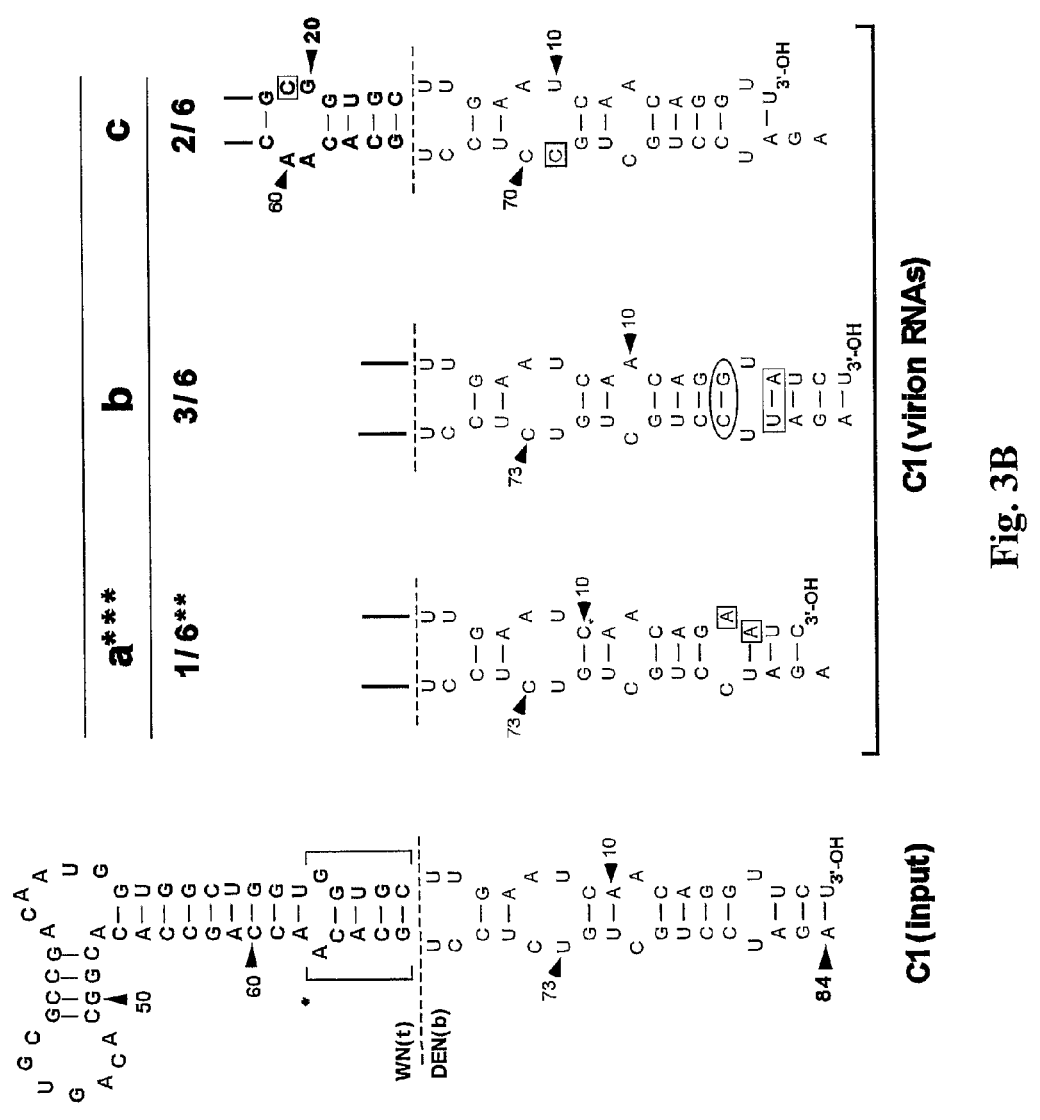

The results of the IFA indicated that all viable 3'SL mutant RNAs were at least slightly less infectious than wt WN virus RNA, based on the time required for transfected cell monolayers to become 100% positive for WN virus antigens (FIG. 2). However, results of the IFA were not necessarily indicative of subtle differences in infectiousness due solely to 3'SL mutations among and between viable mutant RNAs, because some of them were generated by transcription from cloned mutant DNAs and some from full-length PCR products. This variable could have artifactually skewed the kinetics of the IFA. To resolve this issue, an infectious center assay was conducted in which the specific infectivity of mutant RNAs derived from cloned recombinant plasmid DNAs and of mutant RNAs derived from PCR product DNAs was compared to that of wt RNAs derived by each of the two methods. Results of two independent experiments in BHK cells are shown in Table 1. Wt RNA derived from the WN virus recombinant plasmid DNA (and used in the IFA) had a specific infectivity of $33.4 \times 10^3$ and $26.4 \times 10^3$ PFU/µg, respectively, in the two experiments, whereas the specific infectivity of wt RNA derived from a full-length wt PCR product DNA was $10.0 \times 10^3$ and $12.0 \times 10^3$ PFU/µg, respectively, in the same two experiments. For WNmutE RNA, which was also generated by both methods, there was a similar relationship in specific infectivity between RNA derived from cloned plasmid DNA ($18.0 \times 10^3$ PFU/µg in one experiment) and RNA derived from PCR product DNA ($8.0 \times 10^3$ and $5.0 \times 10^3$ PFU/µg in two experiments). The specific infectivity of WNmutC1 RNA was comparable to that of wt RNA, despite the fact that replication of C1 virus was associated with spontaneous mutation of the C1 3'SL (FIG. 3B). This indicated that the input C1 3'SL nucleotide sequence was quite functional for recruitment of factors required to initiate replication. RNAs derived from PCR product DNAs might have been slightly less infectious than those derived from cloned DNAs due to premature termination of transcription of PCR-derived templates or due to random lethal mutations introduced into a subpopulation of DNAs during PCR. In any case, the difference in specific infectivity observed between wt RNAs derived by the two methods and between the respective wt RNAs and relevant mutant RNAs (Table 3) was much less than an order of magnitude in all cases and differences did not rise to the level of statistical significance.

The infectious center assay was more sensitive for detecting small differences in specific infectivity between mutant RNAs derived from PCR-product DNAs and those derived from cloned DNAs than was the IFA. However, wt and all viable mutant RNAs were markedly contrasted with lethal mutant RNAs (WN/DN-SL, -A1, -A2, -A4, and -C2), all of which failed to induce the synthesis of detectable WN virus antigens after 20 days of observation postelectroporation. This indicated a fundamental difference in functionality of the 3'SLs in wt and viable mutant RNAs compared to that of lethal mutant RNAs, regardless of the method of derivation.

Kinetics of Replication of Viable Mutant Viruses in BHK and C6/36 Cells

The kinetics of the replication of wt and viable mutant viruses in BHK and C6/36 cells was determined at an MOI of 0.01 each case, using amplified and plaque-titered stocks. The 3' termini of the genomes of viruses used in this assay were analyzed to verify the presence of the respective mutant 3'SL nucleotide sequences shown in FIG. 3B through 8. WNmutC1 virus contained the C1b 3'SL nucleotide sequence (FIG. 3B.) Plaque titers were determined daily for virus secreted into the medium for 8 or 9 days, and results are shown in FIGS. 9 and 10 and Table 2.

Figure 9:
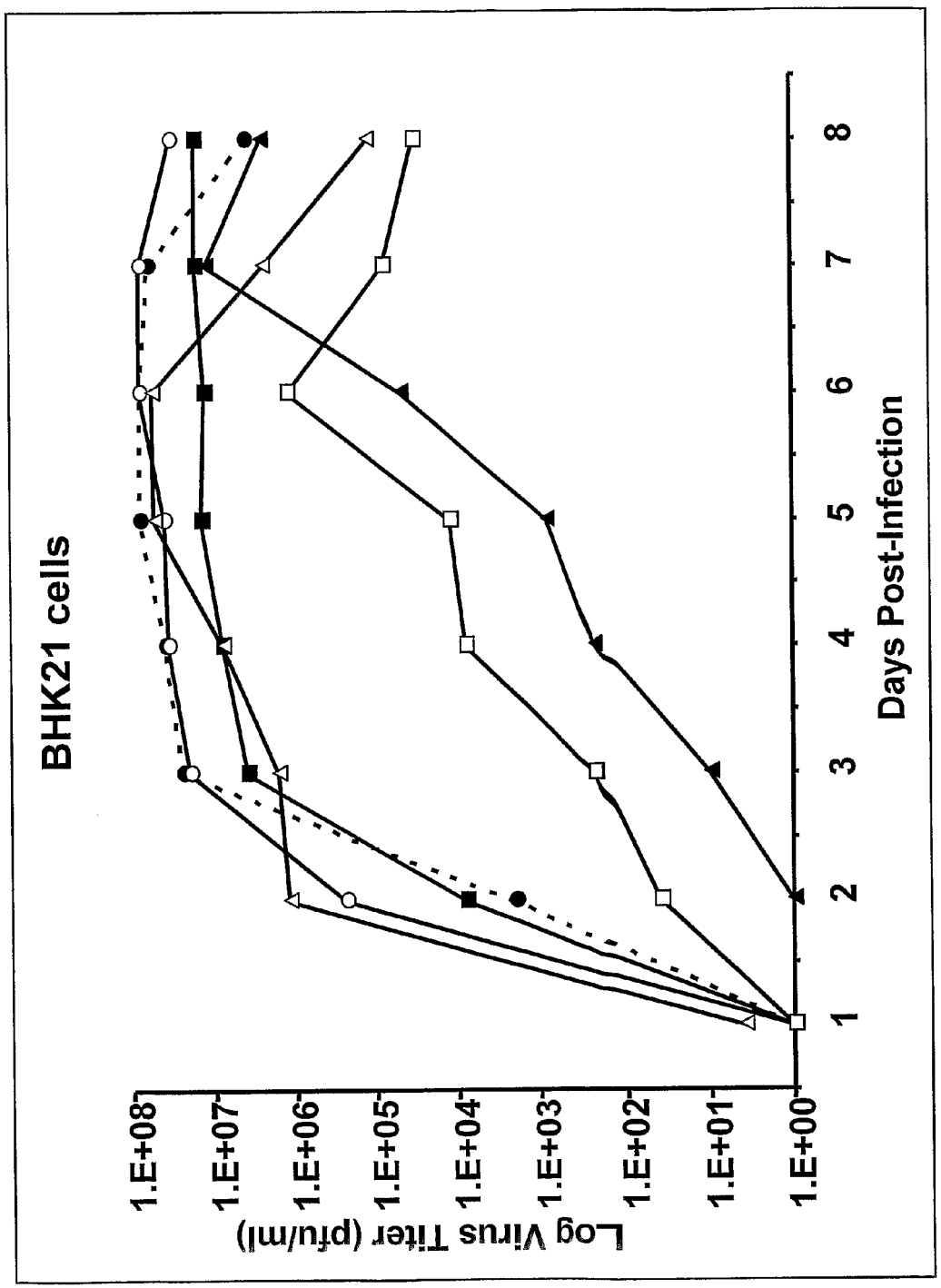
FIG. 9. Replication of viable WN 3'SL mutant viruses in BHK cells. Plaque titers were determined for pools of viruses derived by transfection of BHK cells in Vero cells; these viruses were used to infect confluent monolayers of BHK cells at an MOI of 0.01. Plaque titers were determined for aliquots of the medium on infected cells on Vero cells on the days shown after infection. Results for wt WN virus strain 956, WNmutA1L, WNmutA3, WNmutC1, WNmutE, and WNmutF1 viruses are shown. Solid circles and dashed line, wt WN virus; solid squares, WNmutC1 virus; solid triangles, WNmutE virus; open circles, WNmutF1 virus; open triangles, WNmutA3 virus; open squares, WNmutA1L virus.

The peak titer for wt WN virus in BHK cells was about $8 \times 10^7$ PFU/ml, achieved on day 6 post-infection (FIG. 9 and Table 2). In the same experiment, WNmutA3 and WNmutF1 viruses were similar in their peak titers compared to wt virus, whereas the titers of WNmutC1 and WNmutE viruses were about 10-fold lower. We noted that the replication of WNmutE virus was markedly retarded compared to wt WN virus at early times after infection, despite the fact that it ultimately attained a peak titer approaching that of the wt. For example, on day 4 the titer was about 100,000-fold lower than that of wt WN virus and most of the other mutant viruses (FIG. 9). The kinetics of replication of WNmutA1L virus were similar to those of WNmutE virus in the first 6 days postinfection. However, the peak titer of WNmutA1L virus never exceeded $1.2 \times 10^6$ PFU/ml, nearly 100-fold lower than that of the wt (FIG. 9 and Table 2). Therefore, substitution of the WN virus nucleotides forming the double-loop structure atop the long stem by analogous DEN2 nucleotides had a slight negative effect on replication competence of the virus that was not obvious from results of the IFA or the infectious center assay performed after transfection to assess the RNA.

Figure 10:
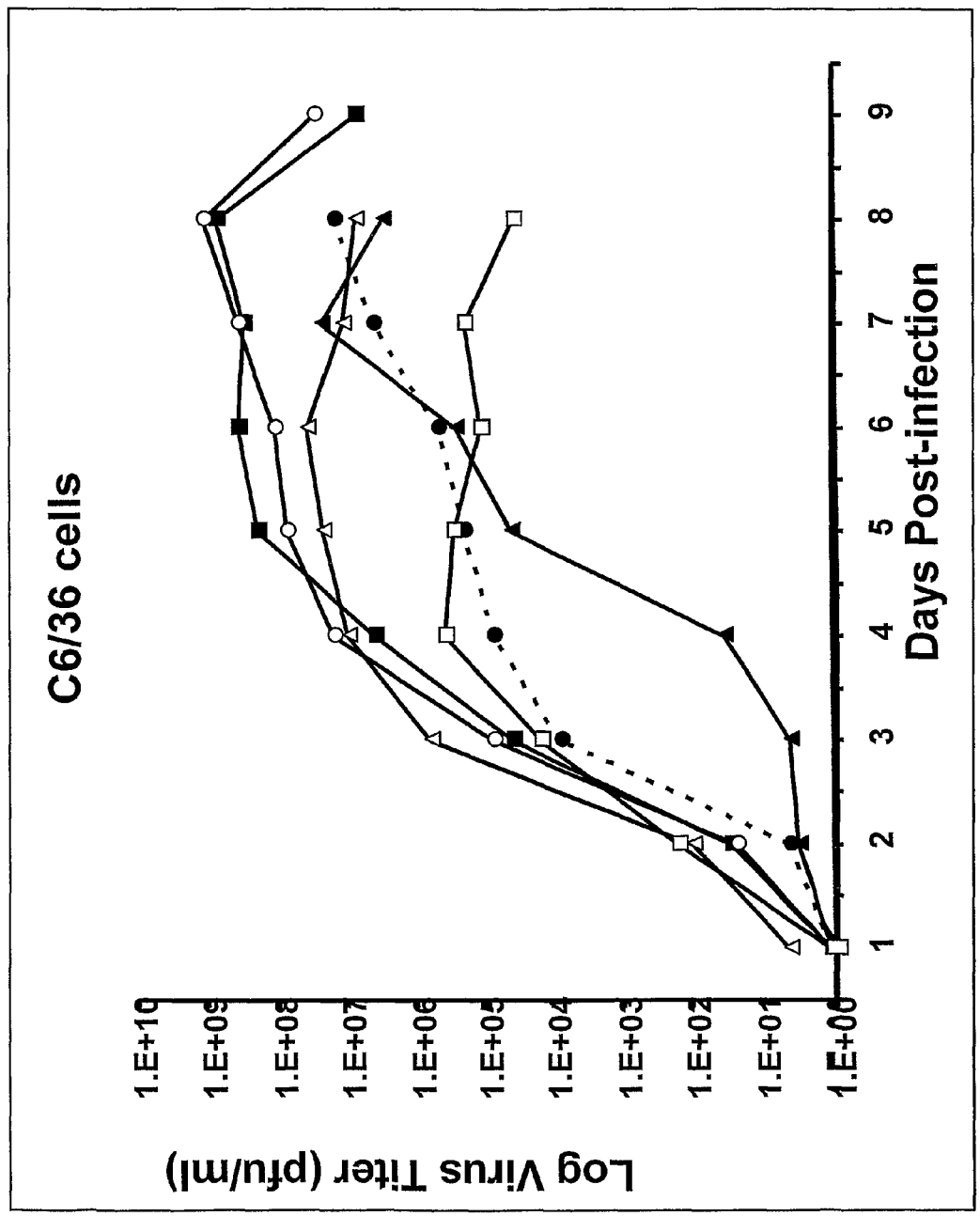
FIG. 10. Replication of viable WN 3'SL mutant viruses in C6/36 cells. Plaque titers were determined for pools of viruses derived by transfection of BHK cells in Vero cells; the viruses were used to infect confluent monolayers of C6/36 cells at an MOI of 0.01. Plaque titers were determined for aliquots of the medium on infected cells on Vero cells on the days shown after infection. Results for wt WN strain 956 and WNmutA1L, WNmutA3, WNmutC1, WNmutE, and WNmutF1 viruses are shown. Solid circles and dashed line, wt WN virus; solid squares, WNmutC1 virus; solid triangles, WNmutE virus; open circles, WNmutF1 virus; open triangles, WNmutA3 virus; open squares, WNmutA1L virus.

The peak titer for wt WN virus in C6/36 cells was about $1.2 \times 10^7$ PFU/ml, achieved on day 8 post-infection (FIG. 10; Table 2). WNmutA3 and WNmutE viruses achieved similar peak titers of $4 \times 10^7$ PFU/ml and $2.5 \times 10^7$ PFU/ml, respectively, even though WNmutA3 virus replicated more vigorously than wt virus at early times after infection, for example on days 3 through 6. In contrast, the replication of WNmutE virus was retarded at early times after infection compared to wt virus, as was observed after infection of BHK cells. The kinetics of replication of WNmutA1L virus in C6/36 cells paralleled that of wt virus up to day 4 post-infection, when the titers of both viruses were about $10^5$ PFU/ml. However, the titer of the mutant virus did not increase after day 4, and therefore the peak titer of WNmutA1L virus was almost 100-fold lower than that of the wt virus.

Figure 8:
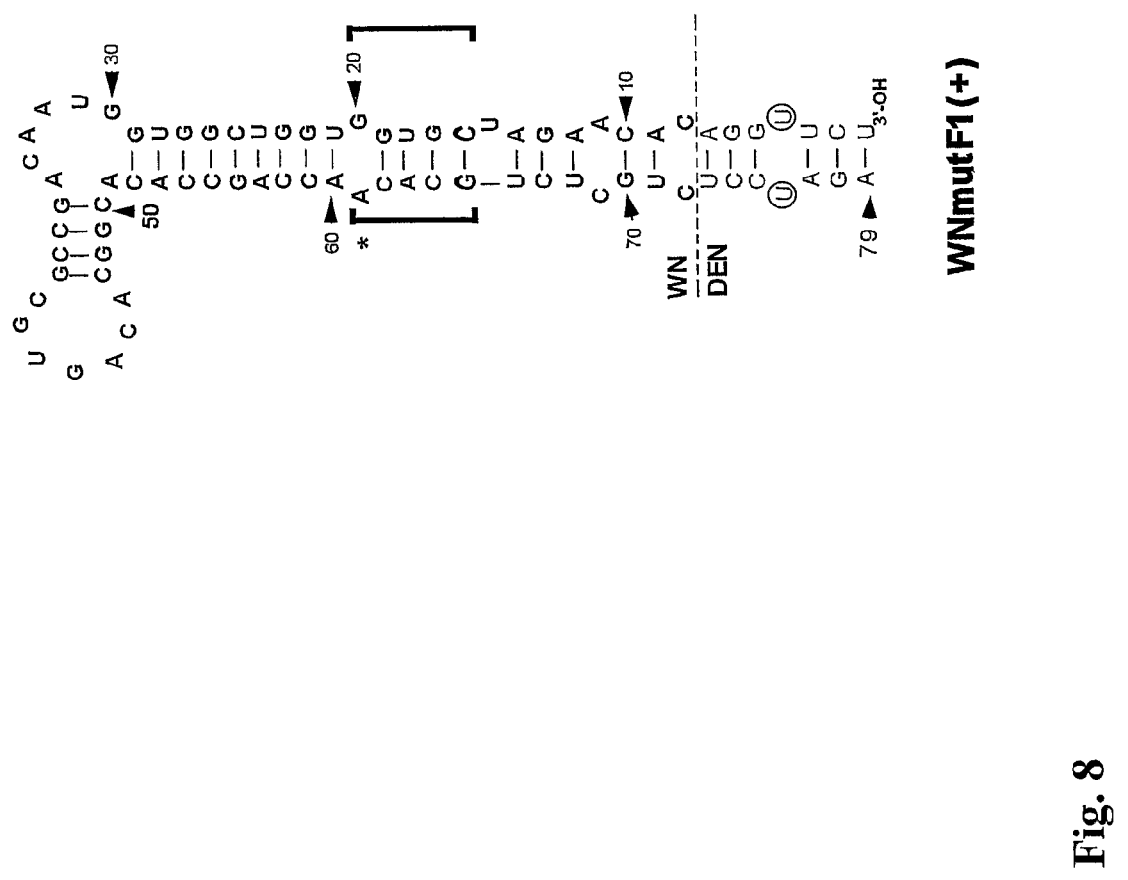

Surprisingly, the peak titers of WNmutC1 and WNmutF1 viruses in C6/36 cells exceeded that of wt WN virus by about 80 and 100 fold, respectively. On day 8 post-infection, WNmutC1 virus reached a peak titer of $8 \times 10^8$ PFU/ml, and WNmutF1 virus reached a peak titer of $1.2 \times 10^9$ PFU/ml (Table 2). In both mutant genome sequences the lowermost 7 bp of the long stem of the 3'SL was derived from the DEN2 nucleotide sequence (FIGS. 1, 3A, and 8). We inferred that the U-U bulge introduced in the context of the 7-bp DEN2-specific segment was mosquito cell growth enhancing for both WNmutC1 and WNmutF1 viruses. Thus, we tentatively identified a second locus in the long stem of the 3'SL where the presence of a bulge resulted in altered growth properties of WN virus.

Complete Genome Sequences of Viable Mutant WN Viruses

As mentioned previously, the 3'SLs in all viable mutant viruses were sequenced to determine whether the respective mutant nucleotide sequences were stable in replicating virus. Except for the C1 3'SL (FIG. 3B) and for the A61C and G20U genomes (see above), this was shown to be true. In addition to verifying the stability of all 3'SL nucleotide sequences in viable RNAs, we also sequenced the complete genomes of wt and WNmutA1L, -A3, -C1, -E, and -2U viruses after amplification in Vero cells (wt, WNmutA1L, and WNmut2U viruses) or BHK cells (WNmutA3, -C1, and -E viruses), to determine whether any other second-site mutations might have been required for viability. The sequences of these RNAs were then compared to the sequence of the WN strain 956 infectious DNA (Table 3).

wt WN virus RNA contained two mutations that differentiated it from that of the parent infectious DNA. Both were silent mutations, one in the envelope (Env) gene segment (G1968U) and one in NS5 (A9465G), respectively. The G1968U mutation was also detected in the WNmutA1L and WNmutC1 genomes. The A9465G mutation was also detected in the WNmutA3 genome. Since they occurred in the wt genome, these mutations were unlikely to have any relationship to the replication phenotypes of the mutant viruses in question. We similarly discounted the significance of silent mutations detected in the ORFs of the WNmutA3 genome (C309U and U1323C), the WNmutE genome (G7356A and A8076G), and the WNmut2U genome (T6682G). The C1 and E genomes both contained mutations in the premembrane (prM) gene segment that were predicted to result in amino acid changes in prM. In view of the results of the IFA and other data (see below and Zeng, L. et al. 1998 *J Virol* 72:7510-7522) indicating that lethal mutations of the 3'SL abrogate translation initiation and/or RNA synthesis, and since there is no published information to implicate prM in those processes, we doubted that these mutations were compensatory for the presence of the C1 or E 3'SLs, respectively, in the WN genome. Therefore, it remained possible that the A10684G mutation detected in the 3'NCR of both the A1L and E genomes, the C10502U mutation in the A1L genome, and the A7898U sense mutation of the NS5 gene segment in the A3 genome (Table 3) could have been required for replication of these genomes, due to altered function of the respective mutant 3'SLs. There was no correlation between the loci of second-site mutations and the cell type in which the viruses were amplified (Vero versus BHK cells).

Northern Blot Analysis of Negative Strand Synthesis

Figure 11:
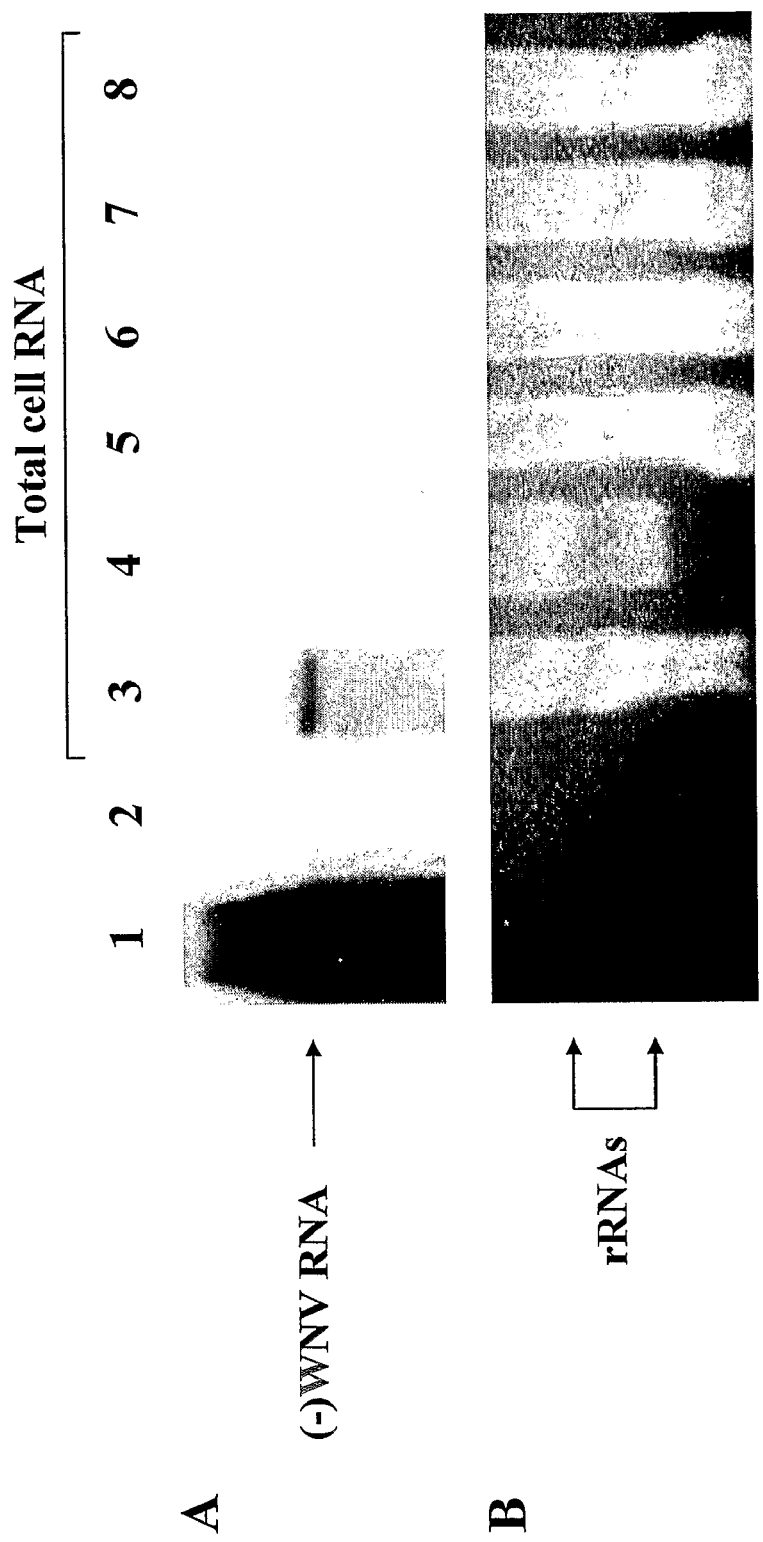
FIG. 11. (A). Northern hybridization analysis of negative-strand WN RNAs in cells transfected by wt and lethal mutant RNAs. Total cellular RNAs were isolated from mock-transfected cells (lane 4) and from cells transfected with wt WN RNA (lane 3) or WNmutA1, WNmutA2, WNmutC2, and WN/DN-SL RNAs (lanes 5 to 8, respectively) 40 hours pos-telectroporation. RNAs were then electrophoresed on a denaturing 1.2% agarose gel for 4 h at 120V, transferred to a membrane, and hybridized to an in vitro-synthesized $^{32}$P-labeled ~4.7-kb positive-sense ssDNA probe representing nt 1894 to 6777 of the WN virus genome. Full-length in vitro-synthesized WN negative-strand RNA (lane 1) and WN positive-strand RNA isolated from infectious virus (lane 2) served as controls to establish the specificity of the hybridization for WN virus negative-strand RNA. (B). After electrophoresis and prior to transblotting, the agarose gel was stained with ethidium bromide and photographed on a UV light box to visualize 18S and 28S rRNAs in preparations of total cellular RNA (lanes 3 to 8).

To evaluate further the defect in replication of lethal mutant RNAs, we conducted a Northern blot analysis of total cellular RNA harvested from cells after transfection with wt and lethal mutant RNAs, using a radiolabeled, positive-sense ssDNA probe (FIG. 11A). The probe was WN negative-strand RNA specific in that it strongly hybridized to a full-length negative-strand WN RNA synthesized in vitro (lane 1) but did not hybridize at all detectably to positive-strand WN RNA harvested from infectious virus (FIG. 11A, lane 2) or to RNA harvested from mock-transfected BHK cells (lane 4). The probe was able to detect genome-size negative strands in cells that had been transfected with wt WN RNA transcripts (lane 3), but no negative-strand RNA was detected in cells transfected by WNmutA1, WNmutA2, WNmutC2, and WN/DN-SL RNAs (lanes 5-8, respectively). rRNAs were visualized in the gel by ethidium bromide staining (FIG. 11B) to establish that roughly equivalent amounts of total cellular RNA were loaded onto the gel. We could not rule out the possibility that very small amounts of negative-strand RNA beneath the level of sensitivity of our assay were present in cells transfected by mutant RNAs that failed to replicate, but the results were consistent with our hypothesis based on the IFA results and previous work (Khromykh, A. A. et al. 1998 *J Virol* 72:7270-7279; Khromykh, A. A. et al. 1999 J Virol 73:9247-9255; Khromykh, A. A. et al. 2000 *J Virol* 74:3253-3263; Zeng, L. et al. 1998 *J Virol* 72:7510-7522) that lethal mutations of the 3'SL abrogated replication at either the level of translation of input virion RNAs or initiation of RNA synthesis. This was consistent with the hypothesis that at least some of the lethal mutant 3'SLs were unable to recruit factors necessary for one or both processes.

Confirmation of the Phenotypes of Lethal Mutations in the WN Virus 3'SL

To reduce the possibility that a technical or procedural error could account for the observed lethal phenotypes of the WNmutC2, WNmutA1, WNmutA2, and WNmutA4 mutations, each transfection experiment was repeated three times with identical results. In addition, to reduce the possibility that we had introduced an occult lethal mutation into the wt WN virus DNA during mutagenesis, we rescued lethal mutants WNmutC2, WNmutA1, and WNmutA2 by replacing the 3'-terminal 508-nt sequence of the respective mutant DNAs with that of wt WN virus, using a technique analogous to that described above for rescuing the prototype WN/D2-SL mutant virus genome. We also recreated C2, A1, and A2 DNAs by PCR, using 3' primers containing the respective mutant 3'SL nucleotide sequences and WNdl16 DNA as template, as also described previously for confirmation of the phenotype of WN/D2-SL RNA. The results in all cases confirmed that the lethal phenotypes of the mutant RNAs were due only to the mutations introduced into the respective 3'SL nucleotide sequences.

Discussion

Flavivirus genomic RNAs contain 5'- and 3'-NCRs with lengths of approximately 100 and 400 to 800 nt, respectively. The 3'-terminal 90 to 100 nucleotide of the 3'-NCR is predicted to form a thermodynamically stable stem-loop structure, referred to as the 3'SL (Grange, T. et al. 1985 *FEBS Lett* 188:159-163; Mohan, P. M. and R. Padmanabhan 1991 *Gene* 108:185-191; Rice, C. M. et al. 1985 *Science* 229:726-735; Wengler, G. and E. Castle 1986 *J Gen Virol* 67:1183-1188). Historical recognition of the 3'SL was based on predictions of folding for only a few hundred nucleotides at the 3'termini of the genomes of various flaviviruses and on digestion of in vitro-synthesized 3'SL RNAs with single- and double-strand-specific RNases (Brinton, M. A. et al. 1986 *Virology* 153:113-121). However, a recent computer-based prediction of the folding of an 8,781-nt Kunjin virus replicon RNA (representing more than 80% of the Kunjin genome) provides confirmation that the 3'SL is likely to be a stable structure in full-length flavivirus RNAs (Khromykh, A. A. et al. 2003 *J Virol* 77:10623-10629). The primary nucleotide sequence of the 3'SL is highly conserved within flavivirus antigenic groups but is not well conserved among or between them. For example, the DEN1 and DEN2 3'SLs share 98% nucleotide sequence homology, but the WN and DEN2 3'SL nucleotide sequences are only 65% homologous (FIG. 1).

The 3'SL secondary structure is required for flavivirus replication (Men, R. et al. 1996 *J Virol* 70:3930-3937; Zeng, L. et al. 1998 *J Virol* 72:7510-7522), but little is known about its function on a molecular level. In vitro studies indicate that the 3'SL binds cellular and viral proteins that may be involved in formation of the replication complex and in translation. For example, short RNA transcripts containing the nucleotide sequence of the WN 3'SL (FIG. 1) bound to the translation elongation factor, eF1-α, in uninfected BHK cellular extracts (Blackwell, J. and M. A. Brinton 1996 *J Virol* 69:5650-5658; Blackwell, J. L. and M. A. Brinton 1997 *J Virol* 71:6433-6444). Similar studies demonstrated binding of eF-1α, PTB, and human La autoantigen to the DEN4 3'SL (De Nova-Campo, M. et al. 2002 *Virology* 295:337-347) and of MOV34, a component of the 26S proteasome that is thought to function in transcription and translation, to the Japanese encephalitis (JE) virus 3'SL (Ta, M. and S. Vrati 2000 *J Virol* 74:5108-5115). Finally, the 3'-terminal 83 nucleotide of the JE genome (the long stem and loop within the 3'SL) competed with full-length JE RNA for binding to virus-encoded proteins, including the viral RNA-dependent RNA polymerase (RdRp), NS5 (Chen, C.-J. et al. 1997 *J Virol* 71:3466-3473), and the virus-encoded helicase, NS3 (Lindenbach, B. D. and C. M. Rice 2001 *Flaviviridae: The viruses and their replication* in Fields Virology, 4th ed., D. M. Knipe and P. M. Howley (ed.), Lippincott Williams and Wilkins, New York pp 991-1041), to form a replication complex. None of the binding sites for cellular proteins (other than for eF1α to the WN virus 3'SL in vitro) or for NS5 have been mapped. These results for flaviviruses parallel other observations on cell protein binding by conserved 3' terminal secondary structures of other positive-strand RNA virus genomes (Huang, P. and M. M. Lai 2001 *J Virol* 75:5009-5017; Ito, T. and M. M. Lai 1997 *J Virol* 71:8698-8706; Nakhasi, H. L. et al. 1990 *New Biol* 2:255-264; Pogue, G. P. et al. 1996 *J Virol* 70:6269-6277).

Results of this and a previous study (Zeng, L. et al. 1998 *J Virol* 72:7510-7522) demonstrated that the complete DEN2 and WN virus 3'SL nucleotide sequences were not interchangeable between the respective genome RNAs. Thus the 3'SL was functionally species or at least flavivirus group specific for replication, and this indicated that nucleotide sequence differences between the DEN2 and WN 3'SLs were critical determinants of replication competence. We investigated this question in relation to WN virus replication by constructing additional mutant WN DNAs that contained chimeric WN/DEN2 3'SLs or point-mutant WN 3'SLs. RNAs derived from these DNAs were evaluated for their ability to produce infectious virus in mammalian kidney cells. Mutant WN RNAs fell into two distinctly different groups; they either replicated nearly as efficiently as wt WN RNA after transfection, or they completely failed to induce the synthesis of both detectable WN antigens and negative-strand RNA in transfected cells. These additional results indicated that failure of the DEN2 3'SL to substitute for the WN 3'SL was due at least primarily to the absence in the wt DEN2 3'SL of a bulge analogous in location to that found in the top portion of the long stem of the WN 3'SL, created by apposition of WN nucleotides A61 and G20 (FIG. 1). Nucleotide A61 in the wt WN 3'SL constituted the 3' terminal nucleotide in a 4-nt sequence shown to be the major in vitro-binding site for eF1-α (Blackwell, J. L. and M. A. Brinton 1997 *J Virol* 71:6433-6444). We therefore defined a 5-bp ds segment that contained the entirety of the eF1-α binding site on one strand as the TEF-binding domain. However, the location of the bulge but not the identity of nucleotides forming the bulge in the long stem of the WN 3'SL was critical for its function. There were three pieces of evidence in support of this idea: (i) all viable mutant RNAs contained a bulge at the site of the A61-G20 bulge in the wt WN long stem or rapidly mutated to restore that bulge; (ii) the bulge in the wt WN long stem could be replaced by a bulged segment (the DRS) (FIG. 1) previously shown to be required for DEN2 virus replication (Zeng, L. et al. 1998 *J Virol* 72:7510-7522), only when the DEN2-specific nucleotides were presented at the locus for the A61-G20 bulge; and (iii) all but two lethal mutant RNAs (A2 and A4) (FIG. 5) lacked the TEF-binding domain, and both of these exceptional mutant 3'SLs contained either extended (A2) or truncated (A4) long stems which altered the locus of the A61-G20 bulge with respect to other elements of the WN virus 3'SL secondary structure.

In summary, nonidentity of the nucleotide sequences of the wild-type WN virus and DEN2 3'SLs did account for the observation that the DEN2 3'SL could not substitute for the WN virus 3'SL in the WN genome, in that the differences in nucleotide sequence resulted in a difference in the topology of the bulges between the DEN2 and WN long stems. A similar hypothesis is possible to explain the previous results for the DEN2 genome (Zeng, L. et al. 1998 *J Virol* 72:7510-7522), since the DEN2-specific 3'SL nucleotides required for DEN2 RNA infectivity (FIG. 1) represent a bulge-rich domain in the long stem of the DEN2 3'SL. We speculate that in general specific bulges in the 3'SL long stem are required for optimal binding of cellular and/or viral proteins essential for flavivirus replication.

Specificity for binding to bulges in the long stem may reside in homo-specific viral proteins required for formation of the replication complex (Khromykh, A. A. et al. 1999 *J Virol* 73:9247-9255; Khromykh, A. A. et al. 2000 *J Virol* 74:3253-3263; Khromykh, A. A. et al. 2003 *J Virol* 77:10623-10629) or for translation of input virion RNAs after uncoating. Alternatively, 3'SL binding specificity may reside in cellular proteins also required for these processes. In the latter case, cellular proteins may recognize the 3'SL in concert with some other part of the genome or in concert with virus-specific proteins, in order to account for failure of the DEN2 3'SL to substitute for the WN 3'SL, and vice-versa. For example, cellular proteins are required to link the 5' and 3' ends of the mouse hepatitis virus and poliovirus RNAs, respectively, to facilitate the formation of panhandle structures as a prerequisite for negative-strand synthesis catalyzed by virus-coded polymerases (Herold, J. and R. Andino 2001 Mol Cell 7:581-591; Huang, P. and M. M. Lai 2001 J Virol 75:5009-5017). Such a model could be applicable to flaviviruses, since there is ample evidence that genome RNA forms a panhandle in the process of flavivirus replication (Khromykh, A. A. et al. 2000 J Virol 74:3253-3263; Khromykh, A. A. et al. 2003 J Virol 77:10623-10629; Lindenbach, B. D. and C. M. Rice 2001 In Fields Virology, 4th ed., D. M. Knipe and P. M. Howley (ed.), Lippincott Williams and Wilkins, New York pp 991-1041).

Our results indicated a functional analogy between the TEF-binding domain and the DRS. Possibly, if the A61-G20 bulge and the three nucleotides upstream from A61 that were previously mapped (Blackwell, J. L. and M. A. Brinton 1997 J Virol 71:6433-6444) are required in vivo for binding eF1-α, then the DRS supports the same function in the context of the DEN2 3'SL, despite the lack of significant nucleotide sequence conservation between the two ds segments. Our results showing that RNAs containing lethal mutant 3'SLs were blocked either for translation of input strands or for negative-strand synthesis are consistent with a model whereby eF1-α is required for initiation of translation, once the 5' and 3'termini of input virion RNAs have been brought together to form a panhandle, and/or for formation of the panhandle in the first place. There are many other equally plausible alternative explanations for our findings related to the binding of viral and/or cellular proteins to the 3'SL. Additional work to identify proteins that bind the 3'SL under physiologic conditions in vivo is contemplated.

The host-range phenotypes of WNmutF1 and WNmutC1 viruses indicated that a bulge in the bottom portion of the 3'SL was relevant to the replication competence of WN mutant viruses in C6/36 cells. Both viruses replicated in BHK cells with an efficiency similar to that of the wt parent WN virus. However, both had a significantly enhanced ability to replicate in C6/36 cells, reaching peak titers about 100-fold higher than that of wt WN virus. The C1 and F1 3'SL nucleotide sequences had in common the substitution of the lowermost 7 bp of the wt WN long stem nucleotide sequence by the analogous domain from the DEN2 3'SL (FIGS. 1, 3A and 8). Within the replaced domain, the WN and DEN2 nucleotide sequences differed primarily in that the DEN2 nucleotide sequence contained a predicted U-U bulge defined by U4 and U76 in the DEN2 3'SL, and the WN virus nucleotide sequence did not. Although the WNmutC1 3'SL underwent spontaneous mutation associated with repeated passaging of C1 virus, the U4-U76 bulge was conserved in the resulting stable C1b 3'SL, although shifted in position by one base-pair (FIG. 3B).

WNmutF1 RNA can be contrasted with DEN2mutF RNA generated in the previous study of the DEN2 3'SL. In DEN2mutF RNA, the U4-U76 bulge was abrogated, because U4 was replaced by A, creating an A-U base pair. DEN2mutF virus replicated only slightly less efficiently than wt DEN2 virus in monkey kidney cells, but it was severely retarded for replication in C6/36 cells (Zeng, L. et al. 1998 J Virol 72:7510-7522). When the growth phenotypes and the secondary structures of the 3'SLs in DEN2mutF and WNmutF1 and C1 RNAs are compared, the combined data indicate that the U4-U76 bulge was an enhancer of DEN2 and WN virus replication specific for C6/36 cells. This could best be explained by postulating that this bulge constitutes a binding site for a protein (or proteins) unique to mosquito cells that functions as part of or assists in formation of the replication complex. Obviously, in the case of wt WN RNA, the U4/U76 bulge is not essential for replication of WN virus to "normal" titers in C6/36 cells.

Several other studies implicate bulged residues in binding of proteins involved in replication of viral RNAs (Weeks, K. M. and D. M. Crowthers 1991 Cell 66:577-588). A bulged loop of unpaired purine residues forms part of the binding site for Qβ replicase in bacteriophage Qβ RNA (Schuppli, D. et al. 1998 J Mol Biol 283:585-593). Binding to RNA of the coat protein of the single-stranded RNA phage PP7 is highly favored by the presence of a single bulged purine residue (either A or G) in the context of an 8-bp hairpin (Lim, F. and S. Peabody 2002 Nucleic Acids Res 30:4138-4144), and the translational operator of the phage R17 replicase gene contains a bulged A residue that is essential for the specific binding to R17 coat protein (Wu, H.-N. and O. C. Uhlenbeck 1987 Biochemistry 26:8221-8227). In brome mosaic virus and tobacco mosaic virus RNAs, 3'-terminal tRNA-like structures axe required for binding RdRp to direct minus-strand synthesis. Mutations that eliminate bulges within these structures disrupt the RdRp/RNA interaction (Chapman, M. R. and C. C. Kao 1999 J Mol Biol 286:709-720; Osman, T. A. et al. 2000 J Virol 74:11671-11680). Binding of the Rev protein to human immunodeficiency virus type 1 RNA and the Rev responsiveness element both require a G-G bulge within a stem-bulge-stem secondary structure. Mutational analysis indicated that Rev binds specifically to the G-G bulge itself (Bartel, D. P. et al. 1991 Cell 17:529-536). In another context, bulges in RNA were apparently necessary to permit shifts in secondary structure required for RNA-RNA or RNA-protein interactions at sites up or downstream from the bulge itself (Kolb, F. A. et al. 2001 Nucleic Acids Res 29:3145-3153).

TABLE 1

Infectious center assays for wt and mutant RNAs in BHK cells

| | Specific infectivity ($10^3$ PFU/μg of RNA) | |
|---|---|---|
| RNA | Plasmid derived[a] | PCR derived[b] |
| Wt | 33.4, *26.4*[c] | 10.0, *12.0* |
| A1L | NA[d] | 2.0, *8.0* |
| A3 | NA | 6.0, *6.0* |
| C1 | 24.0, *19.0* | NA |
| E | 18.0 | 8.0, *5.0* |
| F1 | 30.4, *24.7* | NA |
| 2U | NA | 7.0, *2.0* |

[a]RNA was generated by in vitro transcription from cloned wt or mutant infectious DNAs.
[b]RNA was generated by in vitro transcription from full-length PCR product DNAs.
[c]Results of two separate experiments are shown. Experiment 1 results are shown in plain type; experiment 2 results are shown in italics.
[d]NA, not applicable. The indicated mutant RNA was generated either from cloned mutant infectious DNA or from a PCR product but not both.

TABLE 2

Peak titers of WN 3'SL mutant viruses in BHK and C6/36 cells

| | Peak titer in log pfu/ml (day)[a] | |
|---|---|---|
| Virus | BHK cells | C6/36 cells |
| Wildtype | 7.9 (5) | 7.1 (8) |
| mutA1L | 6.1 (6) | 5.8 (4) |
| mutA3 | 7.9 (6) | 7.6 (6) |
| mutC1 | 7.2 (5) | <u>8.9 (8)</u>[b] |
| mutE | 7.1 (7) | 7.4 (7) |
| mutF1 | 7.9 (6) | <u>9.1 (8)</u> |

[a]Monolayers were infected at an MOI of 0.01 to 0.05 and aliquots of the medium were plaque-titered on Vero cells for up to 10 days post-infection or until lysis of the monolayer.
[b]Results for mutants C1 and F1 are underlined to indicate that peak titers of virus in C6/36 cells exceeded those obtained for wt WN virus by ~100-fold.

TABLE 3

Nucleotide sequence differences between RNA recovered from WN viruses replicating in Vero cells and the WN strain 956 infectious DNA, upstream from the 3'SL[a]

| Virus RNA | nt sequence change | | Codon | AA sequence change | Gene |
|---|---|---|---|---|---|
| | nt number[b] | Mutation | Number | wt AA/sub AA | Segment |
| Wildtype | 1968* | G to U | 624 | (silent) | Env |
| | 9465* | A to G | 3123 | (silent) | NS5 |
| WNmutA1L | 1968* | G to U | 624 | silent | Env |
| | 10502[c] | C to U | NA[d] | | (3'NCR) |
| | 10684 | A to G | NA | | (3'NCR) |
| WNmutA3 | 309 | C to U | 21 | (silent) | Capsid |
| | 1323 | U to C | 409 | (silent) | Env |
| | 7898 | A to U | 2601 | Lys to Thr | NS5 |
| | 9465* | A to G | 3123 | (silent) | NS5 |
| WNmutC1[c] | 511 | G to A | 139 | Ala to Thr | prM |
| | 1968* | G to U | 624 | (silent) | Env |
| WNmutE | 604 | G to A | 170 | Asp to Asn | prM |
| | 7356 | G to A | 2420 | (silent) | NS4B |
| | 8076 | A to G | 2660 | (silent) | NS5 |
| | 10684 | A to G | NA | | (3'NCR) |
| WNmut2U | 6682 | T to G | 2186 | (silent) | NS4A |

[a]DNA sequences from Genbank MI2994 and Yamshchikov, V. F. et al. 2001 Virology 281: 294-304. Mutant viruses contained 3'SL mutations depicted in FIG. 3B through 8 (see text).
[b]Nucleotides are numbered from the 5' terminus of the WN genome. Mutations identified in RNA recovered from wt WN strain 956 virus are indicated by asterisks. nt, nucleotide. Second-site mutations that are possibly required for replication of mutant viruses are indicated by underlining.
[c]The WNmutC1 virus genome contained the C1b 3'SL nucleotide sequence shown in FIG. 3b.
[d]Not applicable

Example 1

Generation of WN Virus DNAs Containing Mutations in the 3'SL

The construction of the pBR322 recombinant plasmid DNA, pSP6WN/Xba, was reported previously (Yamshchikov, V. F. et al. 2001 *Virology* 281:294-304). This DNA contained a full-length infectious DNA copy of a WN virus genome (strain 956). In addition, it contained an SP6 RNA polymerase promoter element upstream from the 5' terminus of WN virus DNA, a unique BclI restriction endonuclease site at WN virus nucleotide (nt) 9833, and a unique XbaI site at the 3' terminus of the WN virus genomic DNA (WN virus nucleotide 10,963; Genbank M12294).

Most mutations of the nucleotide sequence comprising the 3'SL in the WN virus genome (e.g., WN/D2-SL, WNmutC1, WNmutA1, WNmutC2, WNmutA2, WNmutE, and WNmutF1) were created by cloning of PCR fragments containing the desired mutation into wt WN virus infectious DNA. A sense primer, containing the BclI restriction site at nucleotide 9833 (BclI primer: ACCATTTCACGGAACT-GATCATG) (SEQ ID NO: 23), and an antisense primer, containing the nucleotide sequence of the mutant 3'SLs plus the 3' terminal XbaI restriction site, were first used to generate 1.1 kb PCR products, with pSP6WN/Xba DNA used as a template. PCRs were catalyzed by Expand Long Template DNA polymerase (Roche, Indianapolis, Ind.). The mutant PCR products were digested with BclI and XbaI and then inserted by standard cloning procedures with T4 DNA ligase (New England BioLabs, Beverly, Mass.) into pSP6WN/Xba DNA which had been linearized by digestion with BclI and XbaI. To verify the presence of desired mutations in the context of the mutant recombinant plasmid DNAs used to generate infectious RNA, all PCR-amplified regions were analyzed by restriction endonuclease digestion and also sequenced with the Big Dye Terminator kit and an ABI model 377 DNA sequencer (Applied Biosystems, Foster City, Calif.). WN virus recombinant plasmid DNAs containing 3'SL mutations were purified with a Miniprep kit (QIAGEN, Valencia, Calif.) and cleaved with XbaI and used as a template to transcribe viral genomic RNA for transfection assays.

An alternative procedure to produce 3'SL mutant WN virus DNAs involved the amplification of the entire wt WN virus genomic DNA by PCR. For this approach, we utilized an upstream primer: ATGGGTACCATTTAGGTGACACTATA-GAGTAGTTCGCCTGTGAGCTGCA (SEQ ID NO: 24) which contained the SP6 RNA polymerase promoter sequence upstream from the 5' terminal WN virus genomic DNA sequence. Antisense primers complementary to the sequences of mutants WNmutA1, -A2, -C2, -A3, -A4, -A1L, and -E were used to generate the desired 3' terminal mutations in the full-length WN virus DNA PCR products. (Thus, WN virus 3'SL mutants WNmutA1, -A2, -C2, and -E were each generated by both the cloning and full-length PCR methods.) As a template in these full-length PCRs, we used a WN virus DNA that contained a lethal deletion of 16 nucleotide from the 3' terminus of the WN virus genome (WNdl16 DNA) to avoid a false-positive result for infectivity of RNA transcribed from mutant DNAs. Full-length PCR products were generated by 30 cycles of the following program: 95° C. for 15 seconds and 68° C. for 13 min. Reactions were catalyzed by Expand DNA polymerase (Roche) in the presence of a final concentration of 2% dimethyl sulfoxide. Full-length PCR products were purified using a PCR Purification kit (QIAGEN). WNdl16 DNA was also constructed by PCR, as described above using the BclI primer and an antisense primer (TGTTCTAGAACCACCAGCCACCTAT-GTCGGCGCAC) (SEQ ID NO: 25) that introduced a lethal 16-nt deletion mutation at the 3' terminus of the WN virus genomic DNA.

Rescue of Lethal 3'SL Mutations

To regenerate the wildtype WN virus 3'SL nucleotide sequence in the context of mutant WN virus DNAs that were not infectious (e.g., mutants WN/D2-SL, WNmutA1, WNmutA2, WNmutA4, and WNmutC2), the wildtype WN virus 3' terminal BclI/XbaI DNA segment was amplified by PCR, with pSP6WN/Xba DNA as template. Primers used were the BclI primer (see above) and an anti-sense primer representing the complement of wildtype 3' terminal nucleotide sequences (CCTTTCTAGAGATCCTGTGTTCTCG-CACCACCAGCC) (SEQ ID NO: 26). The wildtype BclI/XbaI PCR product was then used to replace each of the respective mutant BclI/XbaI fragments in WN/D2-SL, WNMutA1, A2, A4, and C2 DNAs, as described above.

RNA Transfection and Indirect Immunofluorescence Assays (IFA) to Detect Virus Antigen Production 3'SL mutant recombinant plasmid DNA (1 µg) linearized by digestion with the XbaI restriction endonuclease, or full-length PCR-derived WN virus DNA containing an upstream SP6 RNA polymerase promoter, was used as the template for RNA transcription catalyzed by SP6 RNA polymerase (Promega, Madison, Wis.), as previously described (Zeng, L. et al. 1998 *J Virol* 72:7510-7522). Briefly, template DNAs were incubated with 20 U of SP6 polymerase for 2 h at 40° C. in 30 µl or 60 µl of 1× buffer supplied by Promega and in the presence of 0.5 mM ATP, 0.5 mM UTP, 0.5 mM CTP, 0.1 mM GTP, 5' cap analog ($m^7$G[5']ppp[5']G; New England Biolabs), and 40U RNasin (Promega). Approximately 0.5 µg of RNA transcripts were transfected into a continuous line of BHK21 or Vero cells by electroporation. RNA was added to $10^6$ cells suspended in 300 μL of phosphate-buffered saline (PBS). Cells and RNA were incubated on ice for 10 min prior to electroporation at 200 V and 850 μF in a Gene Pulser cuvette with a 0.4-cm electrode gap, with a Gene Pulser II Electroporator with a capacitance extender (Bio-Rad, Hercules, Calif.). Transfected cells were then plated in one 35-mm-diameter well of a six-well tissue culture plate and fed with Eagle's minimal essential medium (MEM) containing 10% fetal bovine serum (FBS).

An indirect immunofluorescence assay (IFA) was performed on days 3 and 20 postelectroporation (p.e.) on cells that had been seeded to a 1-cm2 chamber on a slide (LabTek; Naperville, Ill.) on the day of electroporation. In a second type of experiment involving IFA, a transfected cell monolayer (one 25-ml flask) was trypsinized on days 5, 10, 15, and 20 p.e. On each of these days, 1/20 of the total cells were transferred to a 1-cm2 chamber slide, and IFA was performed on this slide 16 h later. Each time this procedure was performed, the remaining cells were replated in fresh medium. For IFA, a 1:50 dilution in PBS of WN virus hyperimmune mouse ascitic fluid (HMAF; American Type Culture Collection; Manassas, Va.) was used to detect viral antigens in acetone-fixed cells. Fluorescein-conjugated goat anti-mouse antibody (Kirkegaard and Perry Laboratories; Rockville, Md.) was used as a detector antibody at the 1:200 dilution. A Leitz Diaplan microscope fitted with a Leica/Wild MPS48 automated photographic system was used for all photomicrographs.

Infectious Center Assay

Approximately $10^6$ BHK cells in a volume of 300 μl of PBS were transfected by electroporation exactly as described above using 0.5 μg of RNA derived by transcription of cloned wt or mutant recombinant plasmid DNAs or 0.1 μg of RNA derived by transcription of wt or mutant full-length PCR product DNAs. In all cases, RNA transcription was catalyzed by SP6 RNA polymerase (Promega), as described above and previously (Zeng, L. et al. 1998 *J Virol* 72:7510-7522). The assays were conducted essentially according to a previously published method (Kummerer, B. M. and C. M. Rice 2002 *J Virol* 76:4773-4784). Briefly, the suspension of transfected BHK cells was mixed with a 5-fold excess of fresh BHK cells, and serial 10-fold dilutions of cells were seeded onto paired wells of six-well tissue culture plates. Plates were incubated for 4 h at 37° C. in 1×MEM. Liquid medium was then removed, and monolayers were overlayered with 1× Earle's balanced salts (Sigma), 1 mM sodium pyruvate (Gibco), 1×NEAA (BioWhittaker; Rockville, Md.), 1× vitamins (Gibco), 2% fetal calf serum and 0.65% Seakem agarose (BioWhittaker). Plates were incubated for 3 days at 37° C. in 5% $CO_2$. Cells were then fixed with 7% formaldehyde for one hour at room temperature. The agarose layer was then removed, and cell monolayers were stained with 1% crystal violet in order to visualize plaques. Wt RNAs derived from cloned plasmid DNA and from a full-length PCR product were titrated in a separate experiment to ensure that the respective amounts used in the assay did not represent an excess. The specific infectivity of RNAs was expressed as the number of PFU per micrograms or RNA.

Plaque Assays of Virus and Determination of Virus Growth Curves

Each of the supernatants derived from transfected BHK21 or Vero cells was harvested when about 70% of the cells were positive for viral antigens, and virus titers were determined by plaque assays on Vero cells. For plaque assays, plates were incubated at 37° C. for 6 to 8 days, and then the monolayer was stained with neutral red for 16 to 18 h. After staining, plaques were counted. To determine a virus growth curve, wt WN virus and each of the viable mutant viruses derived in BHK cells were used to infect both BHK cells in six-well plates and C6/36 cells in T-25 flasks, at a multiplicity of infection (MOI) of 0.01 in each case. Then, 300 μl of supernatant from infected cells was harvested daily for titration. The volume of supernatant removed each day was replaced with fresh medium. Virus titers for each day and each cell line were determined by plaque assay on Vero cells by the method described above.

Sequencing of the 3'SL in Mutant WN Virus RNAs

Virus RNA was extracted from supernatants containing viable mutant viruses to determine the sequences of the respective 3'SLs. A total of 0.4 ml to 1.6 ml of the supernatants harvested from either RNA-transfected cells or from infected cells was centrifuged briefly to remove cellular debris and then mixed with buffer AVL, as supplied by QIAGEN; viral RNA was isolated with a Viral RNA mini-kit (QIAGEN). To determine the nucleotide sequence at the extreme 3' terminus of mutant virus genomes, the 5' cap structure on virion RNA was first removed by incubation at 37° C. for 1 h in a reaction mixture containing 50 mM Na acetate (pH 6.0), 1 mM EDTA, 0.1% 2-mercaptoethanol, 0.01% Triton X-100, 0.2 mM ATP, and 10 U of tobacco acid pyrophosphatase (Epicentre Technologies, Madison, Wis.) in a final volume of 70 μl. After extraction with phenol-chloroform and ethanol precipitation, "decapped" viral RNA was circularized by incubation overnight at 14° C. in a 30-μl reaction volume containing 33 mM Tris-acetate (pH 7.8), 66 mM K acetate, 10 mM Mg acetate, 0.5 mM dithiothreitol, 1 mM ATP, 10% dimethyl sulfoxide, 40 U of RNasin (Promega), and 5 U of T4 RNA ligase (Epicentre Technologies).

A short DNA fragment representing the nucleotide sequence of the 5'-3' junction and upstream and downstream sequences in mutant viral genomes was generated by reverse transcriptase PCR (RT-PCR) with circularized viral RNA as template. RT was primed by an oligonucleotide corresponding to antisense WN virus nucleotide 156 to 130, and PCR was primed by this same primer plus a sense oligonucleotide corresponding to WN virus nucleotide 10437 to 10462 (GenBank M12994). Reaction mixture conditions were essentially as described previously (Zeng, L. et al. 1998 *J Virol* 72:7510-7522), except that in some cases Expand polymerase (Roche) was used instead of Pfu polymerase (Stratagene, Cedar Creek, Tex.) for PCR. Amplified products were sequenced with either one of the RT-PCR primers and with the DNA Sequencing kit (Applied Biosystems), with a model 377 DNA sequence analyzer (Applied Biosystems). Sequencing of complete genomes of wt and viable mutant WN viruses RNA was isolated from 0.5 ml of infected cell supernatant with a virus titer of $10^7$ PFU/ml, with a QIAamp Viral RNA mini-kit (QIAGEN). (In this paragraph, primers listed with lowercase letters indicate negative sense, and uppercase letters indicate positive sense.) RT was performed as described above, with primer 10883D (cctagtctatcccaggtgtcaatatgc) (SEQ ID NO: 27). The full-length RT product was then amplified using primers 1U (AGTAGTTCGCCTGTGTGA-CAAACTTAG (SEQ ID NO: 28), and 2486D (acttccgcaccg-gagctcttgcc) (SEQ ID NO: 29); 2256U (GTGGGGAAAGCCAATACACCAAGTC) (SEQ ID NO: 30) and 4078D (ctttgatgaggcttccaactccaacc) (SEQ ID NO: 31); 3950U (TAAGCTTCACCAACACTTCAAATGTG) (SEQ ID NO: 32) and 5337D (tgaggtttggtaccgaatgggaagtc) (SEQ ID NO: 33); 4426U (AGAGTAGATGTGAGGCTG- GATGATG) (SEQ ID NO: 34) and 8700D (catcgtggtcacattggtgatagtg) (SEQ ID NO: 35); 8626U (GCCAGCTCCCTTGTGAATGGGGTAG) (SEQ ID NO: 36) and (10883D). PCR products representing amplified subregions of the WN virus genome were purified with a Qiaquick PCR Purification kit (QIAGEN) and sequenced with a Big Dye Terminator DNA sequencing kit (Applied Biosystems) with the primers listed above plus the following primers: 900U (GTTGCAGCTGTCATTGGATGGATGC) (SEQ ID NO: 37), 1424U (GCCCGACGACCGTTGAATCTCATGG) (SEQ ID NO: 38), 3010U (GCCGTCAAGAACAACATGGC) (SEQ ID NO: 39), 5339U (CTTCCCATTCGGTACCAAACCTCAGC) (SEQ ID NO: 40), 5339U (CTTCCCATTCGGTACCAAACCTCAGC) (SEQ ID NO: 41), 7113D (aacgaagtgttgatagtctg) (SEQ ID NO: 42), 7006U (CTTGATCTGCGGCCGGCCACGGCATGG) (SEQ ID NO: 43), 9975D (cagccacatctgcgcgtatgacttcg) (SEQ ID NO: 44), and 10867D (tgtcaatatgctgtttcttttggtgttt) (SEQ ID NO: 45). Sequence analysis was done with an ABI DNA Sequencer, model 3100, version 3.7 (Applied Biosystems) and Sequencher software (Gene Codes Corp., Ann Arbor, Mich.) on a Macintosh G4 computer.

Northern Blotting for Negative Strand WN Virus RNA in Transfected Cells

Two micrograms of each in vitro-synthesized RNA was added to $5\times10^6$ BHK cells suspended in 300 µl of PBS, and cells were electroporated as described above. Transfected cells were then plated in a 10-cm diameter culture plate and incubated at 37° C. for up to 40 hours in Eagle's MEM with 10% fetal bovine serum. Medium was discarded, and 1 ml of Trizol (Invitrogen) was added to each plate to lyse cells. Total cellular RNA was extracted according to the Invitrogen protocol, for use in preparation of the blot. To generate a negative-sense WN virus RNA for use as a control, WN virus DNA was cloned into the plasmid vector pRS424 (Sikorski, R. S. and P. Heiter 1989 Genetics 122:19-27) between the ClaI and NotI restriction endonuclease cleavage sites in the polylinker segment. The resulting pRS424/WN recombinant DNA was linearized by digestion with ClaI, and a full-length negative-sense copy of the WN virus genome was transcribed from the DNA with T3 RNA polymerase (Promega) for 1 h at 37° C. Positive-strand WN virus RNA for use as a control was isolated from virions (~$5\times10^6$ PFU in 0.5ml), as described above. Approximately 5 ng each of positive- and negative-stranded control RNAs and ~5 µg each of total RNAs isolated from transfected cells were alcohol precipitated and resuspended in 40 µl of denaturing buffer containing 1×MOPS (morpholinepropanesulfonic acid), 50% formamide, and 2.2M formaldehyde and incubated for 5 min at 65° C. Ten microliters of loading buffer (Ambion; Austin, Tex.) was added to each sample, and samples were loaded onto a 1.2% agarose gel containing 1×MOPS buffer and 2.2M formaldehyde and electrophoresed for 4 h at 120 V. The gel was stained with ethidium bromide, photographed on a UV light box to visualize rRNAs, and RNAs were transblotted to a BrightStar-Plus membrane (Ambion) in 20×SSC (1×SSC is 0.15 M NaCl plus 0.015 M sodium citrate). RNA on the membrane was then cross-linked with a model X-1000 Spectrolinker (Spectronics Corporation; Westbury, N.Y.). To prepare a single-stranded (ss), positive-sense, radiolabeled DNA probe, pRS424/WN DNA was cleaved at nucleotide 6777 of the WN virus genome with the restriction endonuclease SphI. Linear DNA was heat denatured at 100° C. for 10 min and reannealed in the presence of a positive-sense oligonucleotide representing WN virus nt 1894 to 1923 (ACTCCCGCTGACACTGGCCACGGAACGGTG) (SEQ ID NO: 46). DNA synthesis was catalyzed by the Klenow fragment of DNA polymerase I (New England BioLabs) in a 50 µl volume containing 10 mM Tris-HCl (pH 7.5); 5 mM dithiothreitol; 0.25 mM each of dATP, dGTP, and dTTP; 2.5 µM dCTP, and 50 µCi of [$^{32}$P]-dCTP (3000 Ci/mmol; Perkin Elmer, Boston, Mass.) and 5U of enzyme at 37° C. for 60 min. The 4.7-kb radio-labeled product ssDNA was purified with a spin column (Edge Biosystems, Gaithersburg, Md.), and the reaction mixture was denatured by incubation at 98° C. for 5 min. The blot was preincubated in a solution of 5×SSPE (1×SSPE is 0.18 M NaCl, 10 mM NaH$_2$PO$_4$, and 1 mM EDTA, pH 7.7), 5×Denhardt's solution, 50% formamide, 0.1% sodium dodecyl sulfate (SDS), 200 µM rGTP, and 10% denatured salmon sperm DNA (Stratagene) for 3 h at 42° C. and then incubated overnight at 42° C. in the same buffer with the denatured $^{32}$P-labeled WN virus ssDNA probe. The blot was then washed at 68° C., twice in 1×SSC-0.1% SDS and three times in 0.1×SSC-0.1% SDS, and exposed to bioMax MS film (Kodak, Rochester, N.Y.).

Computer Analysis of Wt and Mutant 3'SL Nucleotide Sequences

The predicted secondary structures of DEN2 and WN virus wt 3'SL nucleotide sequences and of the corresponding mutant nucleotide sequences were ascertained with the program RNAdraw, an integrated Microsoft Windows program for RNA secondary structure calculation and analysis (Matzura, O. and A. Wennborg 1996 Computer Applications in the Biosciences [CABIOS] 12:247-249).

Example 2

Mouse Neurovirulence

The neurovirulence of WN virus vaccine candidates was evaluated in an experimental model of adult mice. Adult outbred Swiss mice were inoculated intraperitoneally (ip) with up to $10^6$ pfu of each virus, and mortality was recorded. The mutants chosen for the analysis were WNmutC1 (FIG. 3A), WNmutA1L (FIG. 3A), WNmutE (FIG. 6A), and WNmutA2R (FIG. 11) Controls were wild type WN virus strain NY/99, the virus that is circulating in the U.S., and wild type WN virus strain 956. WN virus strain NY/99 had a LD50 (50% lethal dose) of less than one plaque-forming unit (pfu). None of the viruses (except NY/99) showed any lethality at doses below $10^3$ pfu in these mice. Wild type WN virus strain 956 showed about a 50% lethality at all three doses, $10^3$, $10^4$, and $10^5$ pfu, thus the LD50 is about $10^4$ pfu. The results indicate that WN virus strain 956 is attenuated with respect to the NY/99 strain. None of the 3'SL mutant WN viruses showed any lethality at doses up to $10^6$ pfu in adult mice. Thus, all of them are attenuated with respect to both wild type WN viruses used in the study.

The neurovirulence of WN virus vaccine candidates was further evaluated in neonatal mice. Neonatal mice (4 to 6 weeks of age), a more sensitive test system, were inoculated by the intra-cranial (ic) route with up to $10^6$ pfu of each virus, and mortality is recorded. We have succeeded in testing all viruses at doses up to $10^4$ pfu. At the dose of $10^4$ pfu, only WNmutE exhibited no lethality, meaning its LD$_{50}$ is substantially higher than $10^4$ pfu. All other viruses exhibited at least some lethality at this dose. All 3'SL mutant viruses were attenuated with respect to wild type strains at least to some degree.

The neurovirulence of WN virus vaccine candidates is further evaluated in nude mice. Nude mice, which lack a cell-mediated immune response and thus are a specific test system for an antibody-mediated immune response, are inoculated with up to 10⁴ pfu of each virus, and mortality is recorded.

Example 3

Neurovirulence in Monkeys

WN virus vaccine candidates are tested for neurovirulence in a monkey model of WN virus infection. The objectives of WN virus studies in monkeys are: (1) to evaluate the neurovirulence of various vaccine candidates; (2) to evaluate the immunogenicity of test vaccines; and (3) to evaluate the efficacy of the above mentioned vaccines to protect animals against challenge by wild type WN virus.

While the present invention has been described in some detail and form for purposes of clarity and understanding, one skilled in the art will appreciate that various changes in form and detail can be made without departing from the true scope of the invention. All figures, tables, and appendices, as well as patents, applications, and publications, referred to above, are hereby incorporated by reference.

What is claimed is:

1. A West Nile (WN) virus comprising a mutation in the 3' terminal stem loop secondary structure (3'SL) formed by the most downstream approximately 100 nucleotides (nts) of the viral RNA that reduces neurovirulence of said WN virus, wherein the mutation is a substitution in which nucleotide sequences of the WN 3'SL are substituted for analogous nucleotide segments of DEN1, DEN2, DEN3 or DEN4 3'SL resulting in a WN/DEN hybrid 3'SL.

2. The WN virus of claim 1 further comprising an additional attenuating mutation in the genome.

3. The WN virus of claim 1, wherein said WN virus comprises strain 956 or a chimeric WN virus.

4. The WN virus of claim 3, wherein said chimeric WN virus comprises the capsid and non-structural proteins of a first flavivirus and the pre-membrane and envelope proteins of a second flavivirus, the first flavivirus being WN virus.

5. The WN virus of claim 1, wherein the nucleotide sequences of the WN 3'SL that are substituted are selected from the group consisting of: the entire 3'SL structure of the WN virus corresponding to about bases 1 to 95 numbered from the 3' terminus of the WN genome; the top portion of the 3'SL structure of the WN virus corresponding to about bases 16 to 65; the bottom portion of the 3'SL structure of the WN virus corresponding to about bases 1 to 15 and 66 to 95; the bottom half of the long stem portion of the 3'SL structure of the WN virus corresponding to about bases 1-15 and 66-79; the small stem and loop portion of the 3'SL structure of the WN virus corresponding to about bases 80-95; the uppermost portion of the bottom half of the long stem portion of the 3'SL structure of the WN virus corresponding to about bases 8-15 and 66-72; the lower-most portion of the bottom half of the long stem portion of the 3'SL structure of the WN virus corresponding to about bases 1-7 and 73-79; the double-loop structure atop the long stem of the 3'SL structure of the WN virus corresponding to about bases 29 to 52; and the TEF-binding domain of the 3'SL structure of the WN virus corresponding to about bases 14-20 and 61-66.

6. The WN virus of claim 5, wherein the nucleotide sequences of the WN 3'SL that are substituted are selected from the group consisting of: the double-loop structure atop the long stem of the 3'SL structure of the WN virus corresponding to about bases 29 to 52; and the TEF-binding domain of the 3'SL structure of the WN virus corresponding to about bases 14-20 and 61-66.

7. The WN virus of claim 6, wherein the nucleotide sequences of the WN 3'SL that are substituted are selected from the TEF-binding domain of the 3'SL structure of the WN virus corresponding to about bases 14-20 and 61-66.

8. The WN virus of claim 1, wherein the analogous nucleotide segments are of DEN1.

9. The WN virus of claim 1, wherein the analogous nucleotide segments are of DEN2.

10. The WN virus of claim 1, wherein the analogous nucleotide segments are of DEN3.

11. The WN virus of claim 1, wherein the analogous nucleotide segments are of DEN4.

12. The WN virus of claim 7, wherein a bulge replaces said TEF-binding domain.

13. The WN virus of claim 7, wherein U residues replace A61 and G20, respectively.

14. An immunogenic composition comprising the WN virus of claim 1 and a pharmaceutically acceptable carrier or diluent.

15. A method of inducing an immune response to a WN virus in a patient or animal comprising administering the immunogenic composition of claim 14 to a patient or animal to induce an immune response to a WN virus.

16. The method of claim 15, wherein said patient or animal does not have, but is at risk of developing, a WN virus infection.

17. A method of producing a WN virus immunogenic composition comprising introducing into the 3'SL of said WN virus a mutation that results in decreased neurovirulence, wherein the mutation is a substitution in which nucleotide sequences of the WN 3'SL are substituted for analogous nucleotide segments of DEN1, DEN2, DEN3 or DEN4 3'SL resulting in a WN/DEN hybrid 3'SL.

18. A method of identifying a WN virus vaccine candidate comprising the steps of introducing a mutation into the 3'SL of said WN virus, wherein the mutation is a substitution in which nucleotide sequences of the WN 3'SL are substituted for analogous nucleotide segments of DEN1, DEN2, DEN3 or DEN4 3'SL resulting in a WN/DEN hybrid 3'SL; and determining whether the WN virus comprising said 3'SL mutation has decreased neurovirulence, as compared with a WN virus lacking the mutation.

* * * * *